United States Patent [19]

Thomas et al.

[11] Patent Number: 4,749,647
[45] Date of Patent: * Jun. 7, 1988

[54] POLYMERIZATION-INDUCED SEPARATION ASSAY USING RECOGNITION PAIRS

[75] Inventors: Elaine K. Thomas, Seattle; Dennis E. Schwartz, Redmond; John H. Priest, Everett; Robert C. Nowinski; Allan S. Hoffman, both of Seattle, all of Wash.

[73] Assignee: Genetic Systems Corporation, Seattle, Wash.

[ * ] Notice: The portion of the term of this patent subsequent to Apr. 16, 2002 has been disclaimed.

[21] Appl. No.: 623,838

[22] Filed: Jun. 22, 1984

[51] Int. Cl.$^4$ .................... G01N 33/537; C12Q 1/68
[52] U.S. Cl. ................... 435/6; 7; 436/501; 436/504; 436/538; 436/539; 436/548; 436/827; 526/238.1; 525/904; 536/27; 527/202; 935/78
[58] Field of Search ............... 435/6, 7; 436/501, 504, 436/538, 539, 548, 827; 526/238.1; 525/904; 527/202; 536/27; 935/78

[56] References Cited

U.S. PATENT DOCUMENTS

| | | | |
|---|---|---|---|
| 3,969,287 | 7/1976 | Jaworek | 526/238.1 |
| 4,292,296 | 9/1981 | Parsons, Jr. | 436/539 |
| 4,373,071 | 2/1983 | Itakura | 536/23 |
| 4,469,796 | 9/1984 | Axén | 435/7 |
| 4,474,892 | 10/1984 | Murad | 436/548 |
| 4,486,539 | 12/1984 | Ranki | 436/504 |
| 4,506,009 | 3/1985 | Lenhoff | 436/538 |
| 4,511,478 | 4/1985 | Nowinski | 526/238.1 |
| 4,522,922 | 6/1985 | Carro | 435/7 |
| 4,530,900 | 7/1985 | Marshall | 435/7 |
| 4,609,707 | 9/1986 | Nowinski | 436/541 |

FOREIGN PATENT DOCUMENTS 0044988 2/1982 European Pat. Off. ............ 436/538

*Primary Examiner*—Esther M. Kepplinger
*Assistant Examiner*—Robert Benson
*Attorney, Agent, or Firm*—Bertram I. Rowland

[57] ABSTRACT

Methods and compounds are disclosed for determining the presence, amount of, or association between substances of interest in samples suspected of containing same. The methods are based on the polymerization-induced separation of specifically-bound, reporter-labeled recognition reactants from free, reporter-labeled recognition reactants. The methods described are applicable to any substance for which suitable recognition reactants exist or can be made and are not limited by considerations such as chemical composition or molecular size.

35 Claims, 18 Drawing Sheets

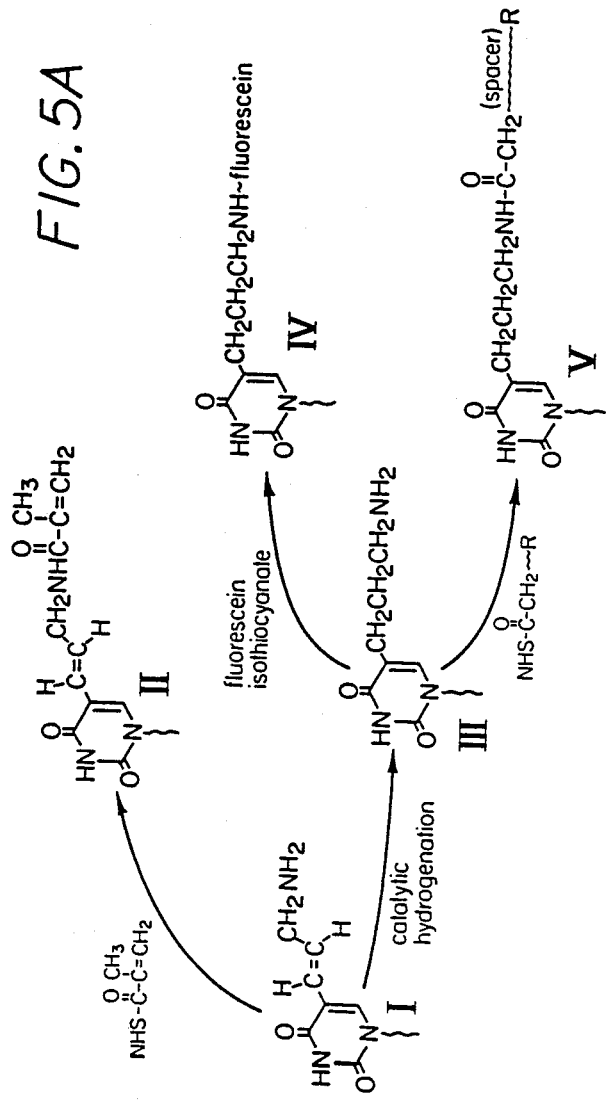
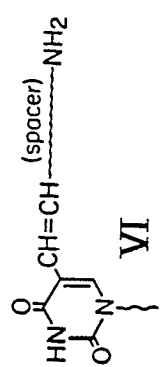
FIG. 5A
FIG. 5B

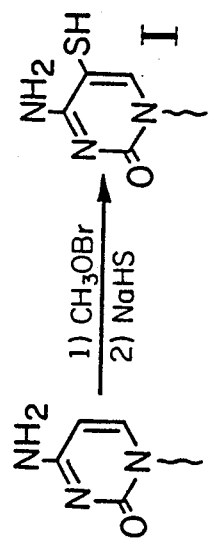
FIG. 6A
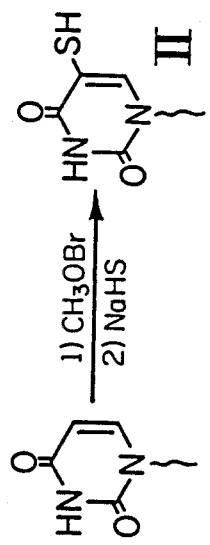
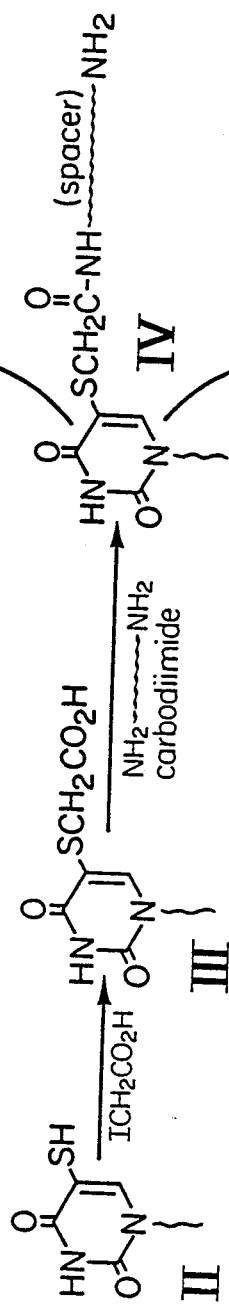
FIG. 6B

FIG. 7A
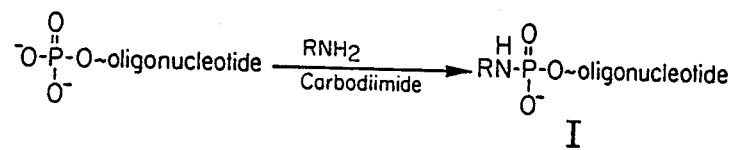
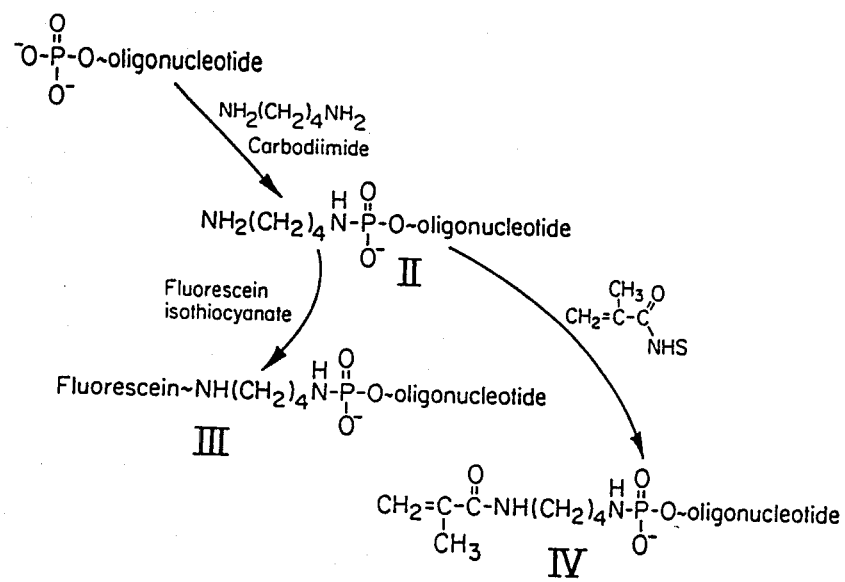
FIG. 7B

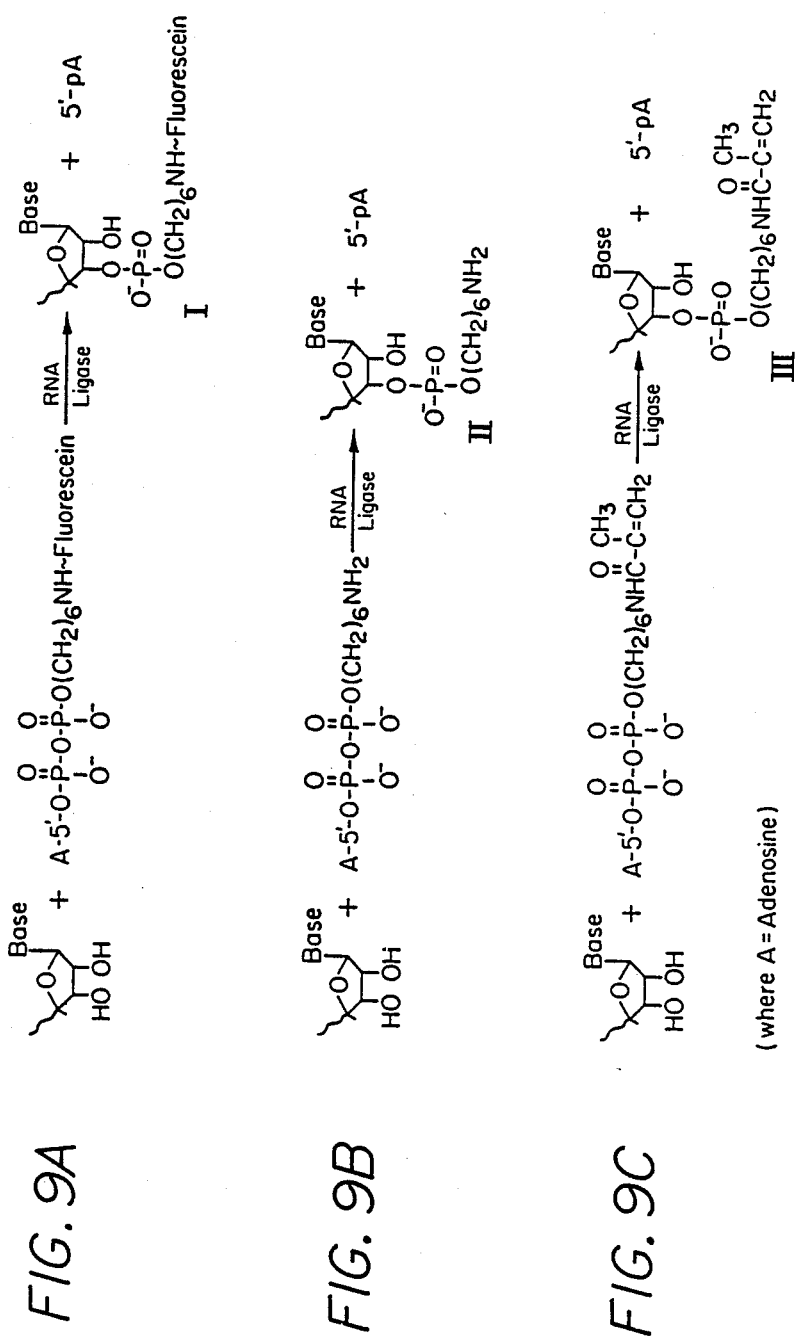

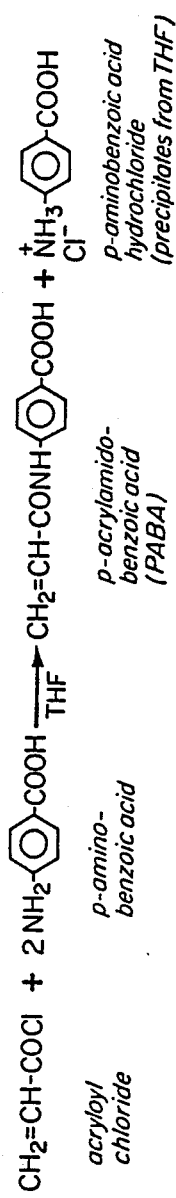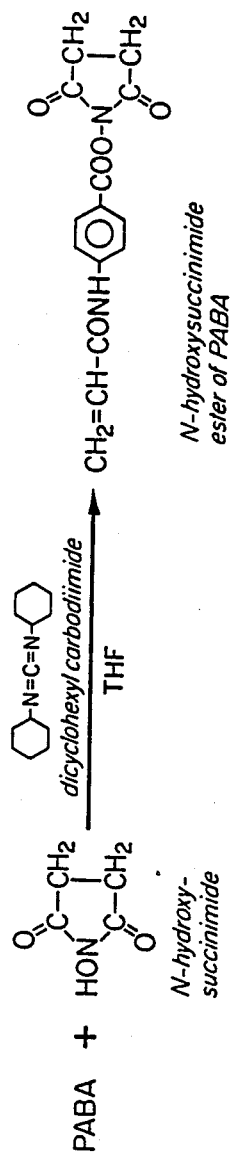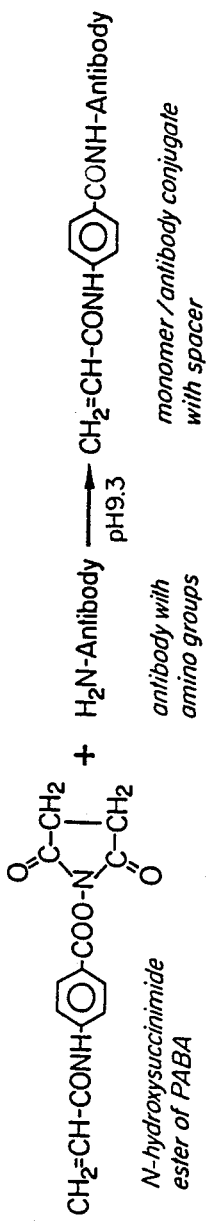
FIG. 16

POLYMERIZATION-INDUCED SEPARATION ASSAY USING RECOGNITION PAIRS

TECHNICAL FIELD

The present invention relates generally to analyte assay methods employing recognition pairs of reactants and more particularly to assays in which a polymerization reaction is used to effect a separation of specifically-bound from free reactants.

BACKGROUND ART

There are numerous disciplines which require assays for the presence of small amounts of organic substances. Illustrative disciplines include disease diagnosis, clinical drug detection and monitoring, food contaminant detection, environmental quality control, and blood screening.

A. Assays

1. Immunoassays

Immunoassays have found widespread application in the field of clinical diagnostics for the detection and measurement of drugs, vitamins, hormones, proteins, metabolites, microorganisms and other substances of interest (analytes) in biological fluids. Typically, these analytes occur in micromolar ($10^{-6}$M) or less concentration.

Immunoassays generally incorporate antibodies and antigens as reactants, at least one of which is labeled with a signal-producing compound (e.g., radioisotope, fluorophore, etc.). Following mixture with the sample and incubation, specific antibody/antigen reactions occur (specific binding). The reaction mixture is subsequently analyzed to detect free and specifically-bound labeled reactant, enabling a measurement of the analyte in the sample.

Immunoassays can be divided into two general categories, homogeneous and heterogeneous. In a homogeneous immunoassay, the signal emitted by the specifically-bound labeled reactant is different from the signal emitted by the free labeled reactant. Hence, bound and free can be distinguished without physical separation.

The archetypal homogeneous immunoassay is the enzyme-multiplied immunoassay technique (EMIT), which is disclosed in U.S. Pat. No. 3,817,837. In this technology, analyte present in patient sample and analyte/enzyme conjugate compete for a limited amount of anti-analyte antibody. Specific binding of antibody to the conjugate modulates its enzymatic activity. Hence, the amount of enzyme activity is proportional to the amount of analyte in the sample. Homogeneous immunoassays have the advantage of being rapid, easy to perform, and readily amenable to automation. Their principal disadvantages are that they are relatively prone to interferences, are generally applicable only to low molecular weight analytes, and are generally limited in sensitivity to approximately $10^{-9}$M.

In a heterogeneous immunoassay, the signal emitted by the bound labeled reactant is indistinguishable from the signal emitted by the free labeled reactant. Therefore, a separation step is required to distinguish between the two.

Typical heterogeneous immunoassays include the radioimmunoassay (RIA) and the enzyme-linked immunosorbent assay (ELISA). In the RIA, radiolabeled analyte and analyte present in patient sample compete for a limited amount of immobilized (solid phase) anti-analyte antibody. The solid phase is washed to remove unbound labeled analyte and either the bound or the free fraction is analyzed for the presence of labeled reactant. ELISA assays are performed analogously. In this case, though, the signal is an enzyme instead of a radioisotope.

Heterogeneous immunoassays typically employ at least one reagent immobilized on a solid phase. Since the kinetics of reaction between an immobilized antibody (or antigen) and its binding partner tend to be slower than the kinetics of the same reaction occurring in solution, long incubation times are frequently required. When the multiple wash steps often needed are taken into consideration, it can be appreciated that heterogeneous assays tend to be time consuming and labor intensive. However, they are in general more sensitive than homogeneous assays and less prone to interferences, since interfering substances can be removed in the wash steps.

Solids used to immobilize reactants in immunoassays have included controlled pore glass and preformed polymers such as polyacrylics, polyacrylamides, polydextrans and polystyrene.

Separation methods used in heterogeneous immunoassays have included centrifugation, filtration, affinity chromatography, gel permeation chromatography, etc.

There is a need in the art for an assay method which is sensitive to sub-micromolar concentrations of analyte; which has fast reaction kinetics; which minimizes the number of manipulations necessary to achieve a result; and which is broadly applicable to analytes of varied chemical composition and molecular size.

2. Nucleic Acid Hybridization Assays

Current methods of diagnosing infectious diseases usually involve detection of bacterial products, particularly genetically encoded products. These products are typically enzymes, which can be detected by biochemical methods, or surface structures, which can be detected by immunochemical methods. In many cases these tests are relatively insensitive and diagnosis may require that large numbers of living microorganisms be present in the sample.

A sensitive and reproducible alternative to detecting gene products as a means of diagnosis is the detection of specific nucleic acid sequences by hybridization to a complementary sequence. Examples of the use of nucleic acid hybridization for the diagnosis of infectious diseases can be found in the following: U.S. Pat. No. 4,358,535; Redfield et al., Diagn. Microbiol. Infect. Dis. 1:117 (1983); Sarkkinen et al., J. Clin. Micro. 13:258 (1981); Moseley et al., J. Inf. Dis. 142:892 (1980); Shafritz et al., NEJ Med. 18:1067 (1981).

Nucleic acid hybridization can also be used, for example, in the prenatal diagnosis of a common form of beta-thallassemia, and sickle cell anemia (Orkin et al., J. Clin. Invest. 71:775 (1983); Conner et al., Proc. Natl. Acad. Sci. USA 80:278 (1983)). These disease states are caused by point mutations. Other genetic alterations such as deletions, insertions, inversions, translocations, transposition of genetic elements, formation of double minutes, restriction site polymorphisms, etc. can also be detected by this method. Presently, gross genetic alterations are detected by karyotyping or by in situ hybridization, while fine structural changes are detected by Southern blotting techniques. It is also possible to demonstrate amplification of genetic information, either at the RNA level or the DNA level, using nucleic acid hybridization. Some or all of the above types of genetic alterations may be important in cancer diagnosis, as well.

While the detection of gene products by immunoassay is quite sophisticated, the detection of the corresponding nucleic acids by hybridization is much slower and more laborious and hence not readily adapted to routine clinical laboratory use. For example, nucleic acid hybridization assays usually require that either the nucleic acid to be detected or the probe for that sequence be immobilized on a solid substrate, typically a nitrocellulose filter, before it is hybridized with the complementary sequence. Unbound (unhybridized) labeled sequences must be physically separated from the assay mixture and the solid substrate washed extensively. Multiple manipulations of the assay mixture are thus required. Also, hybridization is typically slow, usually requiring 4-24 hours. In addition, the time required for autoradiography can extend the length of the analysis to as much as two weeks. Furthermore, little if any of the chemistry developed for non-isotopic labeling of antigens and antibodies has been applicable to nucleic acids.

There is a need in the art for a nucleic acid hybridization assay which is rapid; sensitive; does not require a solid phase; can be non-isotopic; and does not suffer from high levels of background signal.

B. Polymer Chemistry

A reaction fundamental to polymer chemistry is the initiation of covalent linkages between soluble organic monomers (polymerization) leading to the formation of larger polymeric molecular structures (polymers). Synthetic polymers can be formed from a single monomeric species (homopolymer) or from a mixture of different monomers (co-polymer). Linear, branched, or cross-linked structures are possible. By varying the chemical composition or ratios of the monomers, it is possible to form either soluble or insoluble polymers which comprise a broad range of chemical and physical structures. For example, water-soluble monomers (such as acrylamide) can be polymerized to form water-soluble homopolymers. They can also be copolymerized with less water-soluble monomers (such as N-alkyl or N, N-dialkyl acrylamides) or with cross-linking monomers (such as N, N'-methylene bisacrylamide) to form water-insoluble copolymer structures. Some water-soluble monomers (such as hydroxyethyl methacrylate or acrylonitrile) can be homopolymerized to form water-insoluble homopolymers.

In the fields of biochemistry and immunology, water-insoluble polymers (such as polysaccharides and polyacrylics, sometimes cross-linked) have been commonly used as solid phase supports for the adsorption or covalent attachment of proteins in affinity chromatography, enzyme immobilization, and immunoassay. See, for example, U.S. Pat. Nos. 3,957,741; 4,257,884; 4,195,129; 4,225,784; 4,181,636; 4,401,765; and 4,166,105.

Kinoshita, et al. (Progress In Polymer Science VII:63 (1974)) have described the synthesis of vinylated purines and pyrimidines and their free radical-initiated polymerization. The resultant polymers were useful as models for studying nucleic acid biosynthesis.

The coupling of polypeptides to polymers may be performed under conditions in which the polypeptide is provided in soluble form and the polymer is provided as a preformed insoluble material. While these polymers are useful in providing a surface upon which selective biochemical or immunological reactions can occur, it is frequently difficult to attach complex biological molecules to polymers without a concomitant loss of their biological activity. In certain end-use applications where reproducibility and standardization are essential (e.g., immunoassays), this variation in activity of the solid-phase polymer/reactant matrices presents a critical problem. Consequently, there is a need in the art for a method to specifically tailor or molecularly engineer polymer compounds incorporating controlled quantities of reactants.

DISCLOSURE OF THE INVENTION

The present invention provides assay methods for determining the presence or amount of an analyte in a sample suspected of containing analyte. One aspect of the invention provides methods comprising contacting the sample with a first recognition reactant capable of specifically binding to the analyte reactant to form a first recognition reactant—analyte reactant complex. The first recognition reactant is labeled with either a monomer or a reporter. The sample is contacted sequentially or simultaneously with a second recognition reactant capable of specifically binding to the analyte reactant to form a first recognition reactant—analyte reactant—second recognition reactant ternary complex. The second recognition reactant is labeled with either a monomer or a reporter, whichever is not the label for the first recognition reactant. The resultant ternary complex is separated from solution by initiating polymerization or copolymerization of the monomer-labeled recognition reactant. The presence or amount of the analyte is determined by detecting the incorporation of reporter-labeled recognition reactant into the polymerized ternary complex by means appropriate to the reporter.

Another aspect of the invention provides assay methods utilizing monomer/analyte conjugates for competitive assays.

A further aspect of the invention provides compositions of monomer/recognition reactant and monomer/analyte reactant conjugates for use in certain embodiments of the invention.

Another aspect of the invention provides methods for determining an association between two analytes in a sample suspected of containing both analytes. This aspect of the invention comprises contacting the sample with a first recognition reactant capable of specifically binding to the first analyte reactant to form a first recognition reactant—first analyte reactant complex. The first recognition reactant is labeled with either a monomer or a reporter. The sample is contacted sequentially or simultaneously with a second recognition reactant capable of specifically binding to the second analyte reactant to form a second recognition reactant—second analyte reactant complex. The second recognition reactant is labeled with either a monomer or a reporter, whichever is not the label for the first recognition reactant. Polymerization of the monomer-labeled recognition reactant is initiated, whereby the first complex is separated from the second complex unless they are associated. The extent of incorporation of reporter-labeled recognition reactant into the polymerized monomer-labeled complex is directly related to the presence or amount of analyte association.

The polymerization-induced separation assays of the instant invention are believed to offer several advantages over prior art assay methods. Because of the separation achieved by polymerization of the monomer/recognition reactant or monomer/analyte reactant conjugate, the assays of this invention can achieve the sensitivity typical of state-of-the-art techniques combined with ease of performance and low background. The assays of this invention also can typically be performed in less time than traditional assays because binding reactions which would normally occur on a solid phase can be made to occur in solution instead. Also, the need for extensive washing of the solid phase can be reduced or eliminated.

Another unique advantage of the assays of this invention is that they employ as specific reactants sets of recognition pairs. Thus, the range of analytes which can be assayed is limited only by the availability of a suitable recognition reactant for that analyte and not by considerations such as molecular size or chemical nature of the analyte.

BRIEF DESCRIPTION OF THE DRAWINGS

FIG. 5(a) depicts chemical reactions involving 5-(3-amino)allyldeoxyuridine and its hydrogenated product;

FIG. 5(b) depicts an analogue in which the primary amino group is separated from the base by a spacer arm;

FIG. 6(a) depicts chemical reactions leading to the introduction of thiol groups into cytidine or uridine;

FIG. 6(b) depicts the synthesis of 5-thiouridine containing an amino group on a spacer arm;

FIG. 7(a) depicts chemical reactions involving DNA or RNA oligonucleotides having a 3'-terminal ribonucleotide;

FIG. 7(b) depicts the preparation of a DNA oligonucleotide having a single 3'-terminal ribonucleotide and its utilization for the introduction of reporter groups or monomer groups;

FIG. 9(a) depicts RNA-ligase-catalyzed addition of a fluorescein derivative to an oligonucleotide having a 3'-terminal ribonucleotide;

FIG. 9(b) depicts the RNA-ligase-catalyzed addition of a primary amine derivative to an oligonucleotide having a 3'-terminal ribonucleotide;

FIG. 9(c) depicts the RNA-ligase-catalyzed addition of methacrylate to an oligonucleotide having a 3'-terminal ribonucleotide;

FIG. 16 depicts the synthesis of a monomer/antibody conjugate in which the monomer is attached to the antibody via a spacer arm;

BEST MODE FOR PRACTICING THE INVENTION

A. General

Figure 1:
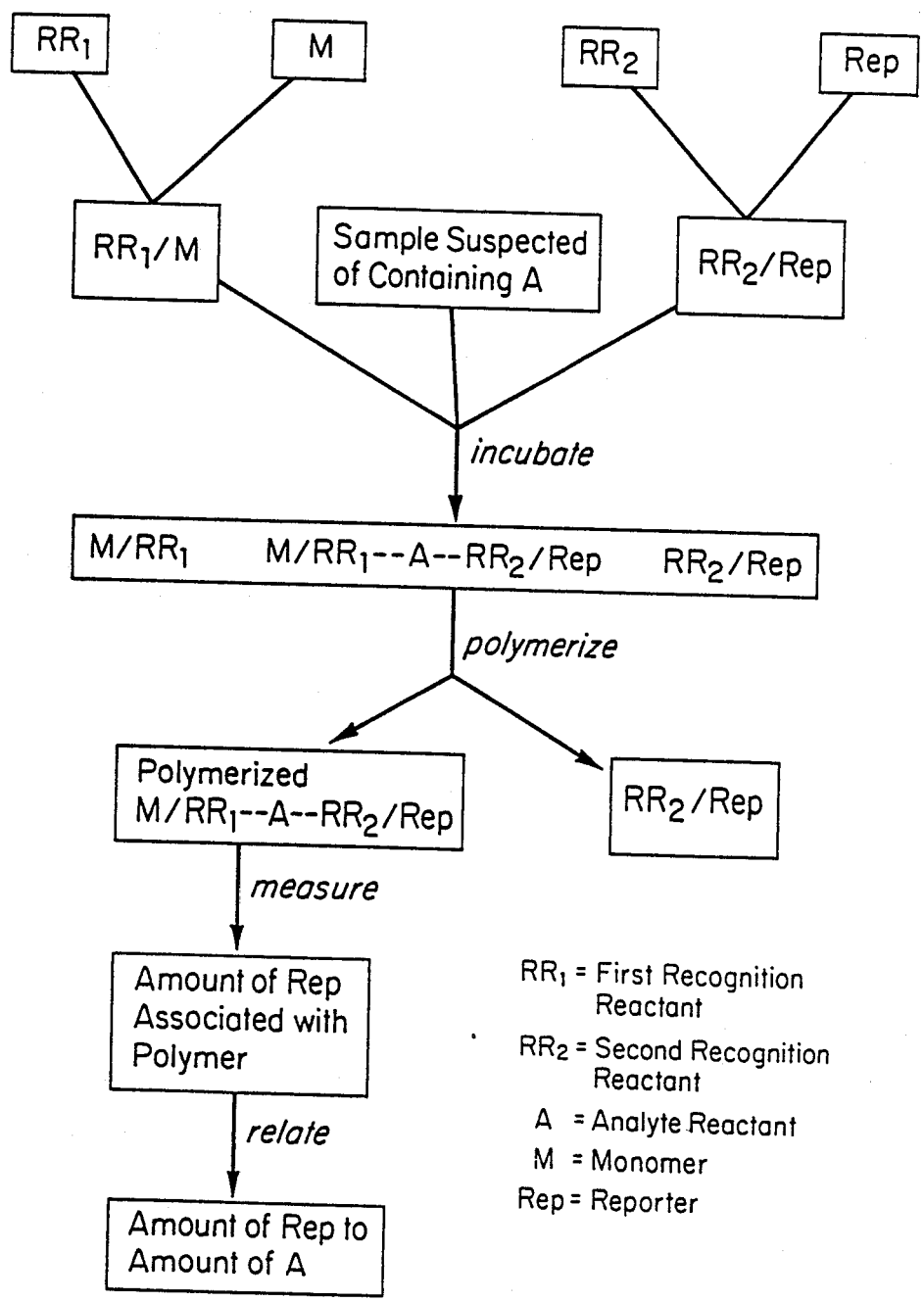
FIG. 1 is a flow chart of a polymerization-induced separation assay performed in a sandwich configuration.

Commonly owned U.S. patent application Ser. No. 550,929 filed on Nov. 10, 1983, discloses methods and compounds for the de novo synthesis of organic polymers that contain antibodies or antigens as an integral part of their backbone structure. This allows one to molecularly engineer polymer compounds incorporating controlled quantities of antibodies for specific applications. Commonly owned U.S. patent application Ser. No. 574,558, filed on Jan. 27, 1984, discloses one such application, namely a polymerization-induced separation immunoassay. The present invention is directed toward the application of this technology to a general method for the detection and measurement of analytes in samples suspected of containing analyte. This invention is not limited by the chemical nature of the analyte (e.g., polypeptide, nucleic acid, steroid, carbohydrate, etc.) nor is it limited by the molecular size of the analyte. The invention can be practiced using any recognition pair of reactants, a recognition pair being comprised of any 2 or more reactants which are capable of specifically binding to each other.

The methods of this invention for the assay of analytes in fluid samples utilize conjugates of reactants with polymerizable organic monomers (monomer/reactant conjugates) or with signal-emitting compounds (reporter/reactant conjugates). Separation of specifically-bound from free reporter/reactant conjugate is effected by a polymerization reaction.

A feature common to biologically active molecules is their capability of interaction (binding) through, for example, hydrogen, hydrophobic, ionic, or polar bonding. These interactions among molecules vary in strength, resulting in a continuum of affinities between different molecules. For example, a particular antibody may interact with a variety of different antigenic structures with an affinity constant that is unique for each different antigenic structure. Based on an ordering of its affinity of interactions, the particular antibody can be said to have a greater specificity for certain binding partners (antigens) as compared to others. This property of affinity and specificity can be exploited to detect and measure the amounts of homologous binding partners in a solution.

Analyte assay methods have been practiced as immunoassays, i.e., assays in which the specific reactants are antigens and antibodies. While the methods of the present invention can also be practiced with antigens and antibodies as the specific reactants, they enjoy the advantage that they can be practiced with other sets of recognition pairs as well. For example, a nucleic acid sequence can be used in a nucleic acid hybridization assay to measure its binding partner, a complementary nucleic acid sequence.

In order to measure the binding of members of a recognition pair in an unknown sample, it is convenient to label one of the reactants (typically the recognition reactant) in the pair with a signal-emitting reporter, such as a fluorophore, radioisotope, enzyme, particle, luminescence source material, etc. This enables sensitive detection of the reporter/recognition reactant conjugate in free or complexed form (i.e., bound to its homologous binding partner, e.g., the analyte reactant). Utilizing different test configurations, such as competitive or sandwich assays, the measure of reporter/recognition reactant conjugate in bound or free form can be quantitatively translated into a measure of the amount of analyte reactant in the unknown sample.

In the method of this invention bound and free recognition reactants are rapidly and conveniently separated by inducing the polymerization of one of the recognition reactants which has been conjugated to a polymerizable organic monomer. Following mixture and incubation with a sample under conditions favoring the specific binding of recognition reactants and analyte reactant, the assay can be rapidly and conveniently concluded by initiating polymerization or copolymerization of the monomerized reactant, resulting in a physical separation of the polymer/reactant from free solution. Should the reporter/reactant conjugate be complexed with the monomer/reactant conjugate, for example, via specific binding to the analyte reactant to form a ternary complex, a one-step partitioning of bound from free reporter/reactant conjugate results.

Advantages of this assay method include the following: (1) Reactions occur in free solution, providing optimal binding kinetics. (2) The assay can be applied to a broad range of analytes (e.g., protein, nucleic acid, steroid, carbohydrate, etc.). (3) The method incorporates advantages of homogeneous assays (e.g., speed and simplicity of performance) with advantages of heterogeneous assays (e.g., physical separation resulting in improved sensitivity and lower background). (4) The method can be used to detect association between analytes.

For the purposes of this disclosure, the following terms are defined: Analyte is the substance or group of substances the presence or amount of which it is desired to determine, including e.g., nucleic acids (DNA or RNA), proteins, steroids, carbohydrates, organic compounds, etc. The analyte typically occurs in a fluid sample, usually a biological fluid; however, other fluids such as, for example, industrial waste streams, are possible. Biological fluids include blood, blood serum, blood plasma; urine; feces; cerebrospinal fluid; saliva; sputum; cells, tissues, and their extracts; extracts of bacterial, viral, fungal, rickettsial, or chlamydial cultures and culture fluids therefrom; umbilical cord blood, amniotic fluid, chorionic villae and cultures thereof, etc. A recognition pair is any two or more reactants which are capable of specifically binding to each other under the appropriate conditions. In the case where the recognition pair is comprised of complementary nucleic acid sequences, the specific binding is accomplished through hydrogen bonding (hybridization) of base pairs. Analyte detecting sequence is a nucleic acid sequence which is complementary in whole or in part to the sequence of the analyte. Probe, as used herein, is a modified nucleic acid sequence comprised of an analyte detecting sequence which can, for example, have one or more attached nucleotide sequences which are not complementary to the analyte or other attached molecules. The term association, as used herein, means physical/chemical association and can include genetic linkage. Associated analytes may be associated via covalent or non-covalent bonds; the covalent bonds may be peptide or phosphodiester bonds and the non-covalent bonds may be ionic, polar, hydrophobic, hydrogen, or a combination thereof. The associated analytes may be attached (bonded) directly to each other or indirectly, via their mutual bonding to an intervening molecule(s). Monomer is any organic compound which is capable of forming covalent linkages (i.e., polymerization) under the appropriate conditions and as used herein includes certain polyunsaturated oligomers. Reporter is any substance which is capable of producing a detectable signal either alone or in combination with other reagents.

The assays of the present invention can be performed in any of several configurations. For illustrative purposes, assays are described in which the recognition pair(s) is composed of antigens and antibodies (immunoassays), or complementary nucleic acids (nucleic acid hybridization assays). However, it will be readily appreciated that the present invention can be practiced using any recognition pair of reactants, such as, e.g., Antigen/Antibody, Hormone/Receptor, Drug/Receptor, Drug/Agonist, Drug/Antagonist, Nucleic Acid/Complementary Nucleic Acid, Vitamin/Transport Protein, Enzyme/Cofactor, Enzyme/Substrate, Enzyme/Product, Enzyme/Inhibitor, Lectin/Sugar, Antibody/Receptor, Organism/Receptor, Growth Factor/Receptor, Chelating Agent/Ion, etc. Furthermore, it will be apparent that assays can be performed using mixed sets of recognition pairs. For example, an assay for a nucleic acid analyte might utilize a labeled probe (i.e., the recognition pair is comprised of complementary nucleic acid sequences) and a labeled antibody, for example, to a particular base in the analyte nucleic acid (i.e., the recognition pair is comprised of an antigen—the base—and an antibody). Likewise, it will be apparent that the interaction (association) between different analytes is amenable to detection and measurement using different sets of recognition pairs. For example, specific DNA/protein interactions (association) can be assayed under the appropriate conditions using a labeled antibody to the protein analyte and a labeled probe for the DNA analyte, one of the two labels being a monomer and the other, a reporter. In general, such determinations require cross-linking of the protein(s) to the nucleic acid and fragmentation of the nucleic acid, prior to assay.

B. Assays

1. Immunoassays

The immunoassays of the present invention can be performed in any of several configurations. In a competitive configuration, sample suspected of containing analyte is incubated with a monomer/analyte reactant conjugate (or alternatively, a reporter/analyte reactant conjugate) and a reporter/recognition reactant conjugate (or a monomer/recognition reactant conjugate). In this case, the recognition reactant is typically an antibody to the analyte. Analyte present in sample and monomer/analyte reactant conjugate compete for a limited amount of reporter/recognition reactant conjugate. Polymerization-induced separation of free from specifically-bound reporter/recognition reactant conjugate enables the detection and measurement of analyte initially present in the sample.

In the competitive configuration, the immunoassays of this invention can be used to measure both monoepitopic compounds (haptens) and multiepitopic compounds. Multiepitopic is meant to include both compounds having more than one unique epitope (antigenic determinant) and compounds having a unique, but repeated epitope. Maximum sensitivity in the competitive configuration is generally attained when the recognition reactant is monovalent (having only one binding site) with respect to the analyte. For example, if the recognition reactant is an antibody, monovalent fragments such as Fab and Fab' can be generated enzymatically (see, e.g., Selected Methods In Cellular Immunology, Mishell et al., eds., W. H. Freeman, New York, 1980). Hybrid cell lines can also be selected which secrete mutant monoclonal antibodies (Yelton et al., J. Exptl. Med. 156:1131, 1982).

In another configuration, the immunoassays of this invention can be performed as sandwich assays. This configuration is appropriate only for multiepitopic analytes. In the forward sandwich configuration, excess monomer/recognition reactant conjugate is incubated with sample suspected of containing analyte. In this case, the recognition reactant is typically an antibody to the analyte. Incubation is carried out under conditions in which specific binding is expected to occur. Following polymerization of monomer/recognition reactant conjugate, excess reporter/recognition reactant conjugate is added to the immunoassay mixture. Typically, the recognition reactant is an antibody which does not compete with the antibody in the monomer/reactant conjugate (i.e., the antibodies are to different epitopes). After an appropriate incubation to allow specific binding to occur, polymerization (or copolymerization) is initiated and the presence or amount of reporter/recognition reactant conjugate specifically bound to the polymer is determined. The polymer particles can be washed if desired to remove any unbound reporter/recognition reactant conjugate. In general, however, it is thought sufficient to simply dilute the reaction mixture 2- to 100-fold prior to measuring the amount of reporter associated with the polymer particles. Similarly, if desired, the polymer particles can be separated from solution and the reporter associated with them eluted prior to detection or measurement.

The order of addition of reagents can also be reversed, i.e., sample suspected of containing analyte can be incubated with reporter/recognition reactant conjugate prior to addition of monomer/recognition reactant conjugate. This configuration is referred to as a reverse sandwich assay. Likewise, sample, reporter/recognition reactant conjugate, and monomer/recognition reactant conjugate can be incubated simultaneously rather than sequentially, in which case the immunoassay is referred to as a simultaneous sandwich. Of the three possible sandwich configurations, the simultaneous sandwich is most preferred because it requires the least number of manipulations. All three configurations, however, offer significant advantages over prior art sandwich immunoassays in that incubation times are shortened and washing steps can be reduced or eliminated.

In a non-competitive configuration, the immunoassays of this invention can be performed by incubating sample suspected of containing analyte with monomer/recognition reactant conjugate (the recognition reactant being an antibody to the analyte) under conditions where specific binding is expected to occur. Reporter/recognition reactant can be added sequentially or simultaneously but in this case the recognition reactant is an antibody to the monomer/recognition reactant—analyte reactant complex rather than to the analyte. Following polymerization-induced separation of free from specifically-bound reporter/recognition reactant, the presence or amount of reporter/recognition reactant specifically bound to the polymer is determined. In this configuration, the first recognition reactant (anti-analyte) can be conjugated to either monomer or reporter. Likewise, the second recognition reactant (anti-first recognition reactant-analyte reactant complex) can be conjugated to either monomer or reporter, whichever was not conjugated to the first recognition reactant. This configuration offers the advantage that both recognition reactants can be employed in excess. Thus, the sensitivity of the immunoassay is not strictly limited by the affinity constants of the reactants. This configuration is also appropriate for both monoepitopic and multiepitopic analytes.

Although in the foregoing discussion, the analyte has been assumed to be an antigen, it will be appreciated that the analyte could also be an antibody, in which case both recognition reactants could be antibodies to the analyte antibody or one of the recognition reactants could be an antigen for the analyte antibody and the other an antibody to the analyte antibody. Also, the analyte can be an immune complex (antigen—antibody complex). Similarly, either of the recognition reactants can be labeled with either a monomer or a reporter.

2. Nucleic Acid Hybridization Assays

The nucleic acid hybridization assays of this invention utilize at least two reactants: an analyte reactant which is a nucleic acid sequence, either RNA or DNA, and at least one (and usually two or more) nucleic acid probes (recognition reactants) which are complementary in whole or in part to the analyte to be detected. Alternatively, one or more antibodies capable of recognizing a particular base, sugar, or internucleotide linkage; a particular nucleic acid conformation; or a particular duplex (double-stranded) structure (RNA:RNA, DNA:DNA, RNA:DNA) can be employed as a recognition reactant.

In the preferred configuration, which is analogous to a sandwich immunoassay, two probes are utilized each of which contains a different analyte detecting sequence, one of which is conjugated to a monomer (monomer/probe conjugate) and the other of which is conjugated to a reporter (reporter/probe conjugate).

Sample suspected of containing nucleic acid analyte is incubated sequentially or simultaneously with monomer/probe conjugate and reporter/probe conjugate under conditions where specific binding (hybridization) is expected to occur. The presence of analyte in the sample serves to bridge monomer/probe conjugate and reporter/probe conjugate. Following polymerization-induced separation of specifically-bound from free reporter/probe conjugate, the presence or amount of reporter associated with the resultant polymer is determined.

In another configuration, monomer/analyte conjugate is utilized in a competitive nucleic acid hybridization assay. Monomer/analyte reactant conjugate and analyte present in the sample compete for a limited amount of reporter/probe conjugate. Following polymerization-induced separation of free from specifically-bound reporter/probe conjugate, the presence or amount of reporter associated with the resultant polymer is determined.

Other assay configurations utilize antibodies in addition to probes. For example, it is possible to make antibodies which will recognize and specifically bind to certain nucleic acid conformations (e.g., Z-DNA) or to a host of naturally-occurring or chemically modified bases, nucleosides, nucleotides, sugar moieties, or internucleotide linkages. Such antibodies can be labeled with monomer or reporter and utilized in an assay to detect hybridization of a probe labeled with the alternative composition and containing, for example, an odd base.

It is also possible to make antibodies to RNA:DNA heteroduplexes which will not bind to RNA:RNA or DNA:DNA homoduplexes (Stollar, Science 169:609, 1970). Thus one can configure an assay in which sample suspected of containing a DNA analyte is exhaustively digested with ribonuclease (RNase) to destroy substantially all the endogeneous RNA in the sample, after which the RNase is inactivated and the sample is allowed to hybridize with an RNA probe complementary to the analyte. The extent of hybridization and hence the amount of analyte present in the sample can then be determined by adding an anti-RNA:DNA antibody labeled with a suitable reporter. Alternatively, an RNA analyte can be detected in an analogous manner using DNase and a DNA probe.

In other configurations, the assays of this invention can be utilized to detect association between two or more analytes. For example, one can assay for genetic linkage between nucleic acid sequences or for specific nucleic acid—protein interactions. To do so, it is generally necessary to fragment the sample nucleic acid first to a suitable size. Furthermore, if nucleic acid—protein interactions are of interest, it is also generally necessary to cross-link any nucleic acid-bound proteins in situ prior to denaturation or treatment with an exonuclease and hybridization. This is typically accomplished by ultraviolet irradiation or cross-linking reagents.

For use in the methods of this invention, probes are chosen so that there is no substantial sequence complementarity between them. In general, they are chosen to bind to linked sequences (0 to about 500,000 base pairs apart, more often 0–10,000 base pairs apart, most often 0–500 base pairs apart) in the analyte; however, the sequences to which the probes bind are not necessarily contiguous, nor are they necessarily non-overlapping. If the probes are double stranded, however, they should be chosen so as not to be substantially overlapping.

If the analyte or either of the recognition reactants (probes) is double-stranded, it is generally necessary to treat that reactant(s) under conditions where the strands will separate, for example, at elevated temperatures, at extremes of pH, or with denaturing solvents or chaotropic agents, prior to performing the assay.

The optimum conditions for carrying out the hybridization assays of this invention are determined empirically and will vary depending on the length of the probes and their GC content. Some of the variables which will affect the rate of hybridization include the assay medium, temperature, concentrations of the specific reactants, ionic strength, agitation, etc. In general, it is desirable to adjust the reaction conditions so as to favor very rapid hybridization. For example, it is known that hybridization occurs more rapidly if an inert polymer such as dextran sulfate is included in the assay medium (Wetmur, Biopolymers 14:2517, 1975). Hybridization can also be accelerated by conducting the assay in a phenol-water emulsion (Kohne et al., Biochemistry 16:5329, 1977). In this latter method, acceleration is apparently achieved by concentration of the DNA at the phenol-water interphase. It should be appreciated that such concentration is not possible with heterogeneous systems employing solid supports, e.g., nitrocellulose.

To facilitate automation of the assays of this invention, it can be desirable to include fractional amounts of solvents such as, for example, formamide, in the assay medium. The temperature at which maximum hybridization occurs varies as a function of the formamide concentration. Hence, it is possible to conduct hybridization assays at a constant temperature, independent of the length and GC content of the probe, by choosing the appropriate concentration of formamide. This concentration can be determined empirically for each probe by electrophoresis of the hybridized probe in polyacrylamide gels containing a transverse gradient of formamide.

Other compounds commonly included in the assay medium are bovine serum albumin (BSA), Ficoll (Pharmacia AB, Uppsala, Sweden), polyvinylpyrrolidone, and ribonuclease inhibitors, such as vanadyl ribonucleosides, placental ribonuclease inhibitor, heparin, hydroxystilbamidine isothyamine, and aurin tricarboxylic acid.

In general, hybridization assays are carried out in the presence of carrier DNA, for example, calf thymus or salmon sperm DNA. This reduces the likelihood of non-specific hybridization. One can also add synthetic polynucleotide homopolymers in addition to or instead of other carrier DNAs to achieve the same effect, i.e., to reduce non-specific hybridization. For example, non-specific hybridization can occur with eukaryotic messenger RNA (mRNA) which generally contains poly(A) at its 3'-terminus. Probes may contain attached sequences composed of a single, repeated nucleotide, e.g., poly(U). Thus eukaryotic mRNA can be expected to hybridize with a poly(U)-containing probe non-specifically, i.e., by virtue of complementarity with the attached sequence rather than with the analyte detecting sequence. Alternatively, poly(A) tails in mRNA can be selectively removed by allowing the sample to hybridize first with oligo(dT) to form an RNA:DNA heteroduplex, then digesting the RNA with an enzyme such as ribonuclease H, which specifically removes RNA in heteroduplex (RNA:DNA) structures.

The sensitivity of nucleic acid hybridization assays, as they are commonly practiced, tends to be limited by the background, that is, hybridization of the probe to sequences other than the sequence of interest. In the preferred configuration, the methods of the present invention are significantly more sensitive than prior art methods because of the requirement that two probes must hybridize in relative proximity to each other before signal can be detected in the polymerized complex.

The background can be further reduced if the analyte nucleic acid is fragmented prior to assay. For example, the probability (P) that a nucleic acid analyte of length $l$ will contain sequences exactly complementary to two probes of lengths m and n is approximated by the following equation:

$$P = (\tfrac{1}{4})^m (\tfrac{1}{4})^n (l-m+1)(l-m-n+1)$$

It follows that the change in probability as a function of $l$ is given by the equation:

$$\frac{P_1}{P_2} = \frac{(\tfrac{1}{4})^{m_1}(\tfrac{1}{4})^{n_1}(l_1 - m_1 + 1)(l_1 - m_1 - n_1 + 1)}{(\tfrac{1}{4})^{m_2}(\tfrac{1}{4})^{n_2}(l_2 - m_2 + 1)(l_2 - m_2 - n_2 + 1)}$$

If $m_1$, $m_2$, $n_1$ and $n_2$ are set equal to 20, the equation simplifies as follows:

$$\frac{P_1}{P_2} = \frac{(l_1 - m_1 + 1)(l_1 - m_1 - n_1 + 1)}{(l_2 - m_2 + 1)(l_2 - m_2 - n_2 + 1)}$$

If $l_1$ is set equal to 50,000 and $l_2$ equal to 200, the probability that $l_2$ will contain sequences exactly complementary to both probes can be calculated to be more than 4 orders of magnitude less than $l_1$. Hence, a decrease of 2 orders of magnitude in the average length of the analyte results in more than 4 orders of magnitude decrease in the probability that both probes will bind to the same fragment. It should be appreciated that this calculation applies to the binding of partially complementary sequences as well.

Methods of fragmenting nucleic acids are wellknown in the art and include mechanical shearing, sonication, irradiation, enzymatic digestion, chemical cleavage, or some combination thereof. Chemical cleaving agents include acid, alkali, and anti-tumor agents, such as bleomycin. Enzymes which can be used include restriction endonucleases and various nucleases, such as DNase I, RNase, micrococcal nuclease, and S1 nuclease, the particular choice being dictated in part by the size fragments desired.

If the nucleic acid is fragmented enzymatically, it may be necessary to inactivate the nuclease(s) before carrying out the hybridization. Micrococcal nuclease is readily inactivated by the addition of $Ca^{2+}$-chelating agents such as, for example, ethylene glycol-bis(2-aminoethylether)-N,N,N',N'-tetraacetic acid (EGTA). Other nucleases can be inactivated by heat, by proteases, by the addition of inhibitors, or by the addition of reagents such as diethylpyrocarbonate.

Fragmentation of the nucleic acid analyte prior to assay reduces the background, which enables the detection of genetic linkage (association between two or more nucleic acid sequences), as well as specific protein interactions with DNA or RNA.

C. Polymerization-Induced Separation

1. Polymerizable Organic Monomers

Monomers useful for labeling reactants in the present invention are typically olefinically or acetylenically unsaturated compounds containing at least one reactable site for coupling to the reactant, or to an intermediate chemical spacer compound. Such compounds can include:

(a) molecules containing olefinic unsaturated groups, e.g.:

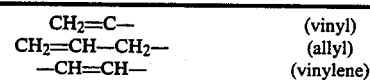

| | |
|---|---|
| $CH_2=C-$ | (vinyl) |
| $CH_2=CH-CH_2-$ | (allyl) |
| $-CH=CH-$ | (vinylene) | and at least one reactable site for coupling to the reactant;

(b) molecules having acetylenic unsaturation, e.g.:

$-C\equiv C-$ and at least one reactable site for coupling to the reactant;

(c) polyunsaturated molecules, containing 2 or more olefinically or acetylenically unsaturated groups, e.g.:

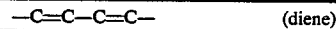

| | |
|---|---|
| $-C=C-C=C-$ | (diene) | and having at least one reactable site for coupling to the reactant.

Monomers which may be used include:

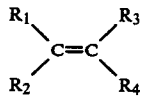

where
$R_1$ and $R_2$ can be H or $-CH=CH_2$
$R_3$ can be $-H$; $-CH_3$; $-Cl$; $-Br$;
$R_4$ can be $-COCl$; $-COOH$ $-COOR_5$ where $R_5$ is $-C_nH_{2n+1}$; with n=1 to 6; $-COOR_6-OH$ where $R_6$ is $-(C_nH_{2n})-$; with n=2 to 6; $-COOR_6-COOH$; $-COOR_6-NH_2$; $-COOR_6-NHR_5$; $-COOR_6N(R_5)_2$; $-COOR_6-NCO$ $-COOR_6-NCS$; $-COOR_6-NHCH_2OH$; $-COOR_6-Cl$; $-CN$;

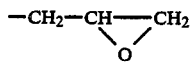

$-CH_2-CH-CH_2$ with O bridging

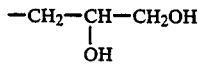

$-CH_2-CH-CH_2OH$
          |
          OH $-R_7NH_2$ where $R_7$ is $-(C_nH_{2n})-$ with n=1 to 6;
$-R_7NHR_5$; $-R_7NHCH_2OH$ $-R_7NCO$
$-R_7NCS$; $-R_7OH$; $-R_7COOH$; $-R_7Cl$;
$-CONH_2$; $-CONHR_5$; $-CONHCH_2CONHR_5$, $-CONHCH_2CONH_2$; $-CONH(CH_2)_nOH$;
$-CONHR_5NH_2$;

$-R_8NH_2$ where $R_8$ is

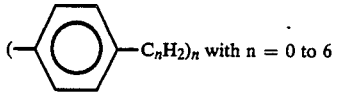

$(-\phantom{}\bigcirc\phantom{}-C_nH_2)_n$ with n = 0 to 6

—R$_8$NHR$_5$;  —R$_8$NHCH$_2$OH;  —R$_8$NCO; —R$_8$NCS; —R$_8$OH; —R$_8$COOH; —R$_8$Cl; —R$_9$—NH$_2$ where R$_9$ is —(OCH$_2$)—; —R$_9$—NHR$_5$; —R$_9$—NCO; —R$_9$—NCS; —R$_9$—OH; —R$_9$—COOH; —R$_9$—COOR$_5$; —R$_9$—COOR$_6$OH; —R$_9$—Cl; —NCO; —NCS; —Cl; —Br; —OCOR$_5$COOH; —OCOR$_{10}$Cl where R$_{10}$ is (CH$_2$)$_n$; with n=0 to 6; —OCOR$_{10}$Br; —OCOR$_5$NCO; —OCOR$_5$NCS; —COR$_{10}$H; —R$_5$COCH$_3$; —OR$_5$Cl; —OR$_5$OH; —OR$_5$H;

Examples of monomers which can be used include acrylic or methacrylic acid, acryloyl or methacryloyl chloride, acrylonitrile or methacrylonitrile, glycidyl acrylate or methacrylate, glycerol acrylate or methacrylate, allylamine, allyl chloride; hydroxy-lower-alkylacrylates, such as 2-hydroxyethyl methacrylate (HEMA) or 3-hydroxypropyl methacrylate, and amino-lower-alkylacrylates, such as 2-aminoethylmethacrylate. Preferred are monomers which are soluble in water or water/polar organic solvent mixtures.

Polymerizable polyunsaturated compounds which may be used include monomers, oligomers, and polymers containing two or more olefinic or acetylenic groups and at least one reactable site for coupling to a reactant, or to an intermediate chemical "spacer" compound. Such polymerizable poly-unsaturated compounds are collectively referred to as monomers for the purposes of this disclosure, although they include certain oligomers or polymers. Oligomers or polymers of the type which may be used include:

(i) Molecules with pendant unsaturation and reactable pendant and terminal groups;

Molecules with pendant and terminal unsaturation and reactable pendant groups;

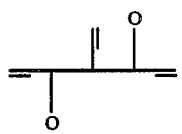

Molecules with both pendant reactable and unsaturated groups;

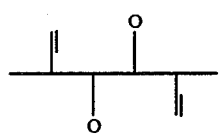

Molecules with pendant unsaturated groups and reactable terminal groups;

Molecules with pendant unsaturated groups, one unsaturated terminal group and one reactable terminal group;

(ii) Molecules with backbone unsaturation and reactable terminal groups;

(iii) Molecules with backbone unsaturation and one eactable terminal group; and

Molecules with one unsaturated terminal group and one reactable terminal group,

where "—" indicates a reactive polar group, "=" indicates unsaturation, and the backbone can include, for example, multifunctional organic compounds; oligo- or polypeptides, nucleotides, saccharides; and oligomers or polymers of polyesters, polyamides, polyvinyls, polyacrylics, polyallyls, polyethers, polyalcohols, polyamines, silicones, polydienes, polycarbonates, etc. The backbone can contain pendant or terminal reactable groups to which pendant unsaturated groups can be added.

The reactable sites on the reactant to which the monomer may be bonded include, for example, covalently bondable functionalities, such as hydroxyl, amide amine, hydrazinyl, acid chloride, isocyanate, isothiocyanate, aldehyde, carboxyl, sulfhydryl, ester, urethane, epoxide, etc.

It is also possible to attach the monomer indirectly to the reactant via an intermediate chemical compound which functions as a spacer arm. Reactable sites on the spacer can include, for example, covalently bondable functionalities, such as hydroxyl, amine, carboxyl, or sulfhydryl groups. Examples of such compounds include ε-aminocaproic acid, 1,4-diaminobutane, 1,6-diaminohexane, 1,4-butanediol, and p-aminobenzoic acid. Possible advantages of the use of spacers are increased incorporation of the monomer/reactant conjugate into the polymer and better reactivity of the reactant portion of the conjugate with its specific binding partner. Both effects are thought to be due to the enhanced accessibility of the conjugate and/or the olefinic or acetylenic groups of the monomer to the bulk solution.

It should be appreciated that substances other than the recognition reactant or the analyte reactant can also be labeled with monomer. For example, in cases where other signal-generating reagents in addition to the reporter-labeled reactant are required, it is possible to monomerize those reagents, whereby they too will be copolymerized into the polymer as it is formed. This results in a large effective increase in concentration of the signal-generating reagents. This effect is expected to be especially useful when the detection system employs coupled enzymes (i.e., the product of the first enzyme in the couple is the substrate for the second enzyme in the couple) or resonance energy transfer (i.e., light emitted by a first component is absorbed by a second component, which emits at a different wavelength), etc. Because of the amplification achieved by physical transfer and concentration of the components of the signal-generating system in the microenvironment of the polymer, the sensitivity of the assay can be dramatically improved.

Other physico/chemical differences between the microenvironment of the polymer and the bulk solution can also affect the signal. For example, the pH in the microenvironment of the polymer may differ from that of the bulk solution, affecting the solubility, fluorescence, or other properties of the signal-emitting compound(s).

2. Polymerization Initiation

Separation of the bound from the free reactants is accomplished by polymerization of the monomer/reactant conjugate. The term polymerization as used herein includes both homopolymerization and copolymerization, as discussed below. Polymerization can be conducted at about room temperature with or without agitation, or it may be advantageous to conduct polymerization at higher temperatures, for example, 37° C. A surface active agent may or may not be present. Although the reaction can be carried out in the presence of oxygen, in some cases it may be preferred to conduct the reaction in the absence of oxygen or in the presence of a controlled amount of oxygen. The pH range may vary widely from about pH 3 to about pH 10, although it is preferable to select a pH where the reactant remains the most stable, for example, typically between pH 6 and 8 for proteinaceous reactants. If a surface active agent is used, suitable compounds, such as sodium dodecyl sulfate, sodium stearate, or nonionic materials, such as polyethyleneoxide lauryl ether (Nonidet P-40), may be employed.

Homopolymerization of the monomer/reactant conjugate with itself or copolymerization with nonderivatized monomers is initiated by generation of free radicals. Nonderivatized monomers which may be used include, for example, ethylenically and/or acetylenically unsaturated monomers, as previously discussed, alkyl or hydroxyalkyl acrylates or methacrylates where the alkyl radical contains from 1 to 6 carbons, acrylonitrile and vinyl acetate, and many others. Also, cross-linking compounds may be co-polymerized with the monomer/reactant conjugate. Such cross-linking compounds may include, for example, N,N'-methylenebisacrylamide or di-, tri- or tetramethacrylates or acrylates. The relative proportions of derivatized and nonderivatized monomer may vary.

The free radicals may be generated by chemical (oxidation-reduction), radiation (light, ultraviolet, gamma, or beta), and/or thermal means. An advantage of oxidation-reduction initiation, ionizing radiation initiation, and light or photochemical initiation is the production of free radicals at reasonable rates at relatively low temperatures, such as ambient (22° C.) or body temperature (37° C.). Types of oxidation-reduction initiators which can be used include (1) peroxides in combination with a reducing agent, e.g., hydrogen peroxide with ferrous ion, or benzoyl peroxide with N, N-dialkylaniline or toluidine, and (2) persulfates in combination with a reducing agent, such as sodium metabisulfite, N,N,N',N'-tetramethylethylenediamine (TEMED), or sodium thiosulfate. Specifically, ammonium persulfate, benzoyl peroxide, lauryl peroxide, t-butyl hydroperoxide, t-butyl perbenzoate, cumene hydroperoxide, or mixtures thereof with reducing agents, such as sodium bisulfite, TEMED, or sodium thiosulfate, may be used. In addition, sodium bisulfite alone may be useful for polymerization.

Photoinitiated polymerization can also be used by employing photoinitiators, such as, e.g., azodiisobutyronitrile, azodiisobutyroamide, benzoin methyl ether, riboflavin, thiazine dyes such as methylene blue and eosin, and transition metals such as ferric chloride or diazidotetramminecobalt (III) azide, in combination with ultraviolet and/or visible light irradiation of the reaction system.

Ionizing radiation may also be employed utilizing radiation from a radioactive source or a particle accelerator.

Polymerization can be carried out in the presence of various physiological materials commonly encountered in biological fluids.

The choice of polymerizing conditions will be influenced to some extent by the chemical nature of the analyte, for example, the conditions which are optimal for protein analytes may differ from those for nucleic acid analytes.

D. Synthesis of Monomer/Reactant Or Reporter/Reactant Conjugates

1. Polypeptide Reactants

Covalent coupling of the monomer to the reactant (be it the recognition reactant or the analyte reactant) or its attached carbohydrate (in the case of glycoprotein reactants) can be carried out by any number of known chemical methods. For example, the monomer and/or the reactant can be activated to produce a stable but reactable intermediate which can be subsequently coupled. The reactant can also be activated by periodate oxidation of the attached carbohydrates, if the reactant is a glycoprotein. This reaction forms aldehydes which can then condense with amino groups on the monomers, such as 2-aminoethyl methacrylate, to form a Schiff base. This Schiff base can be reduced with sodium cyanoborohydride to form a stable covalent linkage. The monomer in the form of an acid anhydride may also be directly coupled with the reactant in the presence of an acid scavenger to remove acid as it is formed during the coupling. Additionally, bifunctional or hetero-bifunctional reagents are known and can be obtained, for example, from Pierce Chemical Company, Rockford, Ill. In almost all cases, the reaction conditions, i.e., time, temperature, solvent and pH, should be such as to avoid denaturation and/or degradation of the reactant.

Methods of coupling the reporter substance to the analyte reactant or recognition reactant are well-known in the art. In general, covalent coupling is preferred, although other means of attachment are possible. The reactive sites which can be utilized for attachment are the same as those discussed above. In general, it is desirable to label the reactant as heavily as possible without loss of binding activity.

A variety of reporter substances are known in the patent and non-patent literature (see, for example, Methods In Enzymology, Vols. 70 & 73, Langone et al., eds., Academic Press, New York, 1981, and references contained therein) and can include, for example, enzymes (such as horseradish peroxidase, glucose oxidase, and β-galactosidase), fluorophores (such as fluorescein, rhodamine, phycoerythrin, phycocyanin and Nile blue), radioisotopes (such as $^{32}P$, $^{3}H$ and $^{125}I$), particles, pigments, luminescence source materials, etc. The reporter alone can be sufficient to generate a measurable signal or additional signal-generating reagents can be required. These may include ions, substrates, cofactors, other enzymes, or other fluorophores. Coupled enzyme systems, enzyme cascades, fluorescent (or chemiluminescent) resonance energy transfer systems, etc. are all possible detection systems; see, for example, U.S. Pat. Nos. 4,220,450 and 4,233,402. The sensitivity of such multi-component detection systems can be enhanced by monomerizing the components (except for the reporter, which cannot be monomerized) so as to transfer and concentrate the components into the polymer as it is formed. If desired, background signal can be reduced by including a scavenger(s) in the bulk solution; see, for example, U.S. Pat. No. 4,252,783.

2. Nucleic Acid Reactants a. Synthesis of Probes

Analyte detecting sequences can be single-stranded or double-stranded RNA or DNA. A variety of methods of synthesizing nucleic acid sequences complementary to given sequences is known in the art. Some representative methods are listed below.

Single- or double-stranded oligonucleotides can be synthesized chemically or enzymatically to correspond to a known sequence. Restriction fragments can be cloned in any of a variety of vectors to produce large amounts of single-stranded or double-stranded sequences. RNA can be transcribed in vitro from DNA using, for example, the SP6 promoter/polymerase system. RNA can be autocatalytically replicated in vitro using, for example, the QB replicase system. Complementary DNA (cDNA) can be synthesized from RNA using reverse transcriptase. Single-stranded sequences can be copied to yield double-stranded sequences. Finally, specific sequences can be purified from natural sources.

Where two or more analyte detecting sequences are required, they can be synthesized by different methods. In general, both analyte detecting sequences should be complementary to the same strand of the analyte, i.e, the plus or the minus strand. However, it is possible under the appropriate conditions to use analyte detecting sequences which are complementary to opposite strands. For example, the nucleic acid to be analyzed can be fragmented with a restriction endonuclease. The resultant fragments can then be treated with a 3'→5' exonuclease, e.g., E. coli exonuclease III, or with a 5'→3' exonuclease, e.g., Lambda exonuclease, to yield fragments which are single-stranded at each end, as shown below.

Analyte detecting sequences can be synthesized which are complementary to the single-stranded ends, one of which will be complementary to the plus strand and the other of which will be complementary to the minus strand.

In the preferred configuration, the assays of this invention utilize two or more probes, at least one of which is labeled with a monomer and at least one of which is labeled with a reporter. In order to preserve base pairing within the analyte detecting sequence, it is usually desirable to restrict labeling to attached sequences which do not contribute to the specificity of the reaction. However, it is possible to label the analyte detecting sequence directly, provided base pairing is substantially preserved.

The analyte detecting sequence together with any attached sequences comprises a probe. Attached sequences can be added to the analyte detecting sequence in any of several ways. For example, the analyte detecting sequence can be (1) tailed with terminal transferase; (2) ligated to a preformed polynucleotide; (3) cloned and replicated in various single- or double-stranded vectors, for example, M13 or pBR322; (4) extended by chemical synthesis; (5) extended by the addition of a non-nucleic acid tail; (6) labeled by nick translation using E. coli DNA polymerase I containing trace amounts of DNase I; (7) extended by a combination of nick translation and terminal transferase tailing; (8) extended by a template-independent RNA polymerase, such as polynucleotide phosphorylase; (9) extended by a template-dependent RNA polymerase such as QB replicase or SP6 polymerase; or (10) hybridized to a pre-formed polynucleotide or polynucleotide/polymer conjugate having a sequence which is complementary to part of the analyte detecting sequence or a sequence attached thereto.

Labeling of the attached sequences with monomer or reporter can be accomplished after the probe has been chemically or enzymatically synthesized (post-synthetic labeling); such probes are hereinafter called class I probes. Labeled bases can also be incorporated directly into the probe during chemical or enzymatic synthesis (synthetic labeling) to produce class II probes. Alternatively, probes can be labeled indirectly as, for example, with antibody to an "odd" nucleotide within the probe; such probes are hereinafter referred to as class III probes.

In any case, the labeled bases should not substantially interfere with the specificity of base pairing within the analyte detecting sequence. The labeled bases must also be acceptable to the relevant synthetic enzymes.

Where class III probes are employed, the probe and labeled antibody can be pre-incubated and added to the assay mixture as a pre-formed complex. Alternatively, the probe and labeled antibody can be added separately to the assay mixture and allowed to specifically bind to each other during the course of the assay or after hybridization is complete. The antibody can be conjugated to either monomer or reporter. The reporter can be a fluorophore, luminescence source compound, enzyme, radioisotope, particle, etc. Methods of making antibody/monomer or antibody/reporter conjugates are described above.

Although the discussion of class III probes has been confined to indirect labeling with antibody, it will be appreciated that other recognition pairs can also be employed. For example, biotinylated bases can be incorporated into the probe and indirectly labeled with avidin/monomer or avidin/reporter conjugate.

Among the methods of synthesizing probes, it is possible to ligate or hybridize the tail of an analyte detecting sequence to a complementary labeled preformed polynucleotide or to chemically introduce a non-nucleic acid tail. The advantage of these methods is that a variety of different analyte detecting sequences can be labeled by hybridization to a single complementary pre-formed polynucleotide. The preformed polynucleotide can be labeled during or after synthesis by any of the methods described below. For example, an analyte detecting sequence having a poly(C) tail can be hybridized to a labeled pre-formed polynucleotide containing a poly(G) tail. To prevent dissociation of the hybridized sequences, the probe can be cross-linked, for example, by irradiation at 365 nm in the presence of psoralen (Hochkeppel et al., Biochemistry 18:2905, 1979).

Below, numerous methods for labeling polynucleotide chains with monomer, reporter, or other groups are described. In general, these methods are based on the introduction of amino, thiol, or carboxyl groups into the nucleotide bases, sugars, or terminal phosphates. These groups are typically more reactive than the nitrogens of the common bases and thus they can be selectively derivatized. In the event that a substantial, undesired modification of one of the common bases (adenine, guanine, cytosine, thymine, uracil) occurs, the reaction conditions can be adjusted to favor derivatization of the desired compound, for example, by decreasing the time of reaction and/or raising the pH of the reaction medium. Alternatively, the common bases comprising the analyte detecting sequence can be protected from derivatization by hybridization to a complementary sequence.

The various labeling chemistries are described first with respect to tailed analyte detecting sequences, then with respect to probes replicated in a vector, for example, M13. However, it will be appreciated that the same chemistries can in general be applied to probes prepared by other methods and in other vectors as well. For simplicity, many of the chemistries are described using methacrylic monomers and fluorescein isothiocyanate as the reporter, however, it will be appreciated that other monomers and reporters can be used as well.

b. Synthesis of Class I Tailed Probes (Post-Synthetic Labeling)

For purposes of illustration, the analyte detecting sequence is assumed to be a short synthetic oligonucleotide, generally 20–30 nucleotides long. Addition of polynucleotide sequences (tailing) is typically accomplished with terminal deoxynucleotidyl transferase (terminal transferase) under conditions such as those described by Deng et al., (Nucl. Acids Res. 9:41, 1981). The resultant sequences will be typically 10–1000 nucleotides in length, more often 25–500 nucleotides in length. The tailed analyte detecting sequence can be separated from untailed analyte detecting sequences or from analyte detecting sequences with short tails ( 25 nucleotides) by gel filtration, or by electrophoretic fractionation on a polyacrylamide gel. This tailing reaction can also be accomplished with ribonucleoside 5'-diphosphates and primer-dependent polynucleotide phosphorylase using either an RNA analyte detecting sequence, or a DNA analyte detecting sequence containing one or more 3'-terminal ribonucleotides.

(1) Deoxy-4-thiothymidine or 4-Thiouridine

Figure 2:
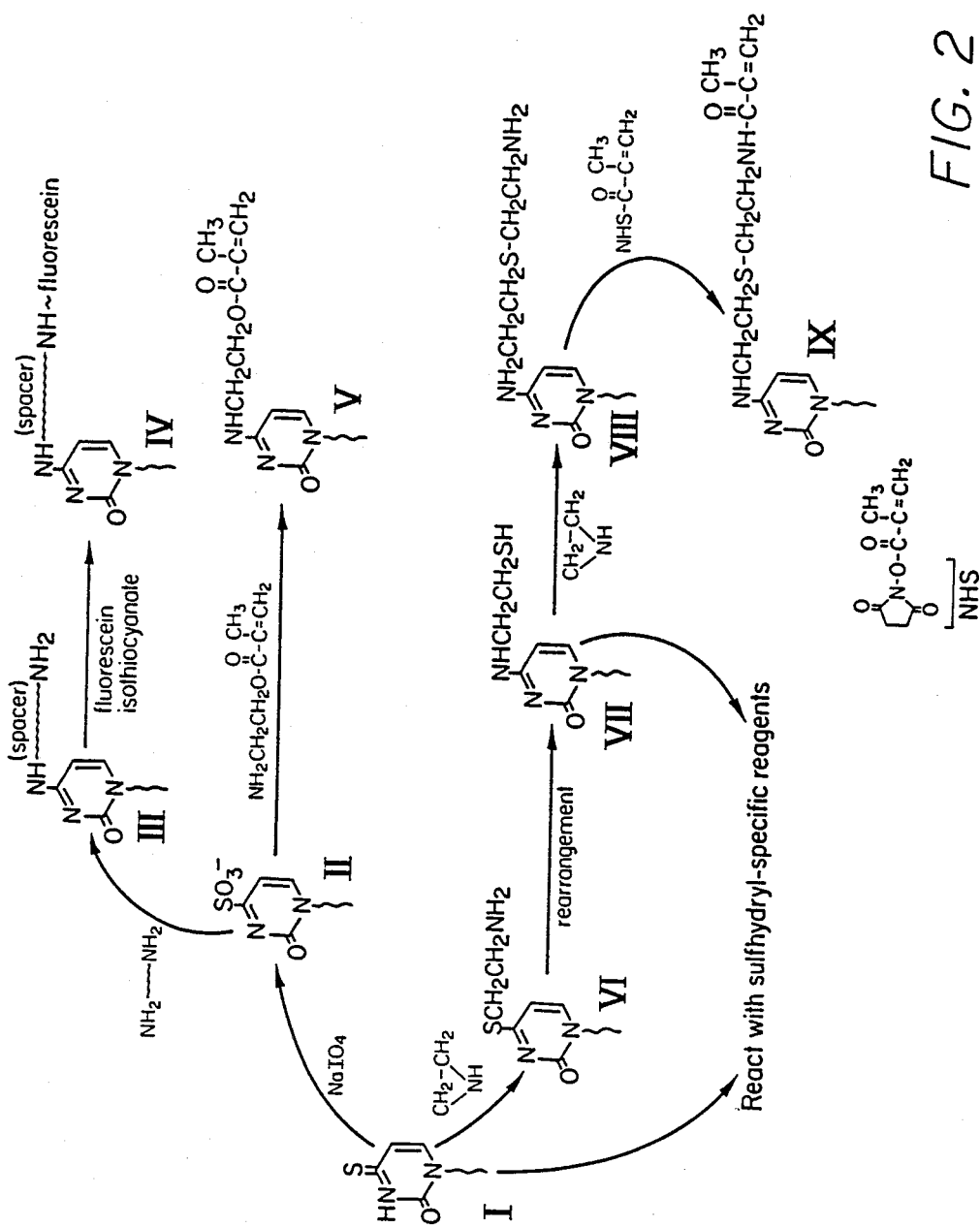
FIG. 2 depicts chemical reactions involving 4-thiouridine.

4-Thiouridine has unusual chemical properties which are useful for chemical derivatization, as shown in FIG. 2. For example, 4-thiouridine (I) can be oxidized with periodate under mild conditions to produce the sulfonic acid derivative (II), which, in turn, can be displaced by a diamine to form the cytidine derivative (III). This compound can then be coupled to form, for example, compound (IV). Alternatively, compound (II) can be treated with a primary amine such as 2-aminoethylmethacrylate to form the cytidine derivative (V).

In addition, 4-thiouridine (I) can be reacted directly with ethyleneimine via a rearrangement reaction to form compound (VII), which then can react slowly with additional ethyleneimine to form (VIII). Which species (VII or VIII) predominates can be influenced by the choice of reaction times. Compound (VII) can be reacted with sulfhydryl-specific reagents. Compound (VIII) can be reacted with primary amine-specific reagents.

4-Thiouridine can also be reacted with iodoacetic acid and the resultant derivative, containing a carboxylic acid, can be coupled to a primary amine in the presence of carbodiimide. Alternatively, compound (I) can be reacted directly to produce an antigenic odd base or can be reacted with a maleimide derivative separated from an N-hydroxysuccinimide (NHS) ester by a spacer. The activated ester group can subsequently be coupled to an alkyl amine.

DNA analyte detecting sequences can be tailed with deoxy-4-thiothymidine 5'-triphosphate via catalysis with terminal transferase. Optimal tailing is generally obtained when polymerization occurs in the presence of one of the major nucleoside 5'-triphosphates. Alternatively, tailing of RNA probes or suitably modified DNA probes can be accomplished with its ribonucleotide analog 4-thiouridine 5'-diphosphate via catalysis with primer-dependent polynucleotide phosphorylase from *Micrococcus luteus*. Although DNA oligomers are not substrates for polynucleotide phosphorylase, DNA oligomers containing one or more 3'-terminal ribonucleotides are substrates. These ribonucleotides can be added to the DNA oligomer most efficiently by carrying out the terminal transferase tailing reaction described above in the presence of 1 mM ATP or GTP (Roychoudhury et al., Nucl. Acids Res. 3:863, 1976). The extended oligomer produced from this reaction contains one to four ribonucleotides and can function as a substrate for polynucleotide phosphorylase-catalyzed addition of attached sequences composed of 4-thiouridine.

For derivatization of 4-thiouridine residues, the following chemistry is illustrated. The resultant probe (1–20 μg) with attached sequences of deoxy-4-thiothymidine or 4-thiouridine is treated with 0.01–0.1 M periodate for 45 minutes at 40° C. The excess periodate is reduced by addition of a two-fold molar excess of ethylene glycol for 15 minutes at room temperature. A suitable primary amine or secondary amine (0.1–0.5 M), e.g., 2-aminoethylmethacrylate (at pH 7–10), is introduced, and the incubation is continued at 40° C. for 30–60 minutes. In some cases, where the primary or secondary amines are not themselves oxidized by periodate, it is possible to carry out the periodate oxidation in the presence of the amine and omit treatment with ethylene glycol. This allows oxidation of the thiol group, with concomitant displacement of the resultant sulfonic acid group by the amine. This one-step procedure gives high yields of substitution (Ziff et al., Biochemistry 8:3242, 1969).

Alternatively, the attached sequences containing the 4-thio derivative can be reacted in one step with ethylenimine to form derivatives VII or VIII shown in FIG. 2. Typically, 1–20 μg of tailed probe is incubated with 0.19M ethylenimine (in 0.2M phosphate, pH 6.8) for 30–60 minutes at 35° C. to form predominantly compound (VII), or for 3–5 hours to form predominantly compound (VIII) (Reid, Biochemistry 9:2852, 1970). The reaction product is separated from excess ethylenimine by ethanol precipitation of the polynucleotides and/or gel filtration on a Sephadex G200 column and then is coupled with the appropriate reagent for introduction of the desired group.

(2) 4-Aminocytidine

Figure 3:
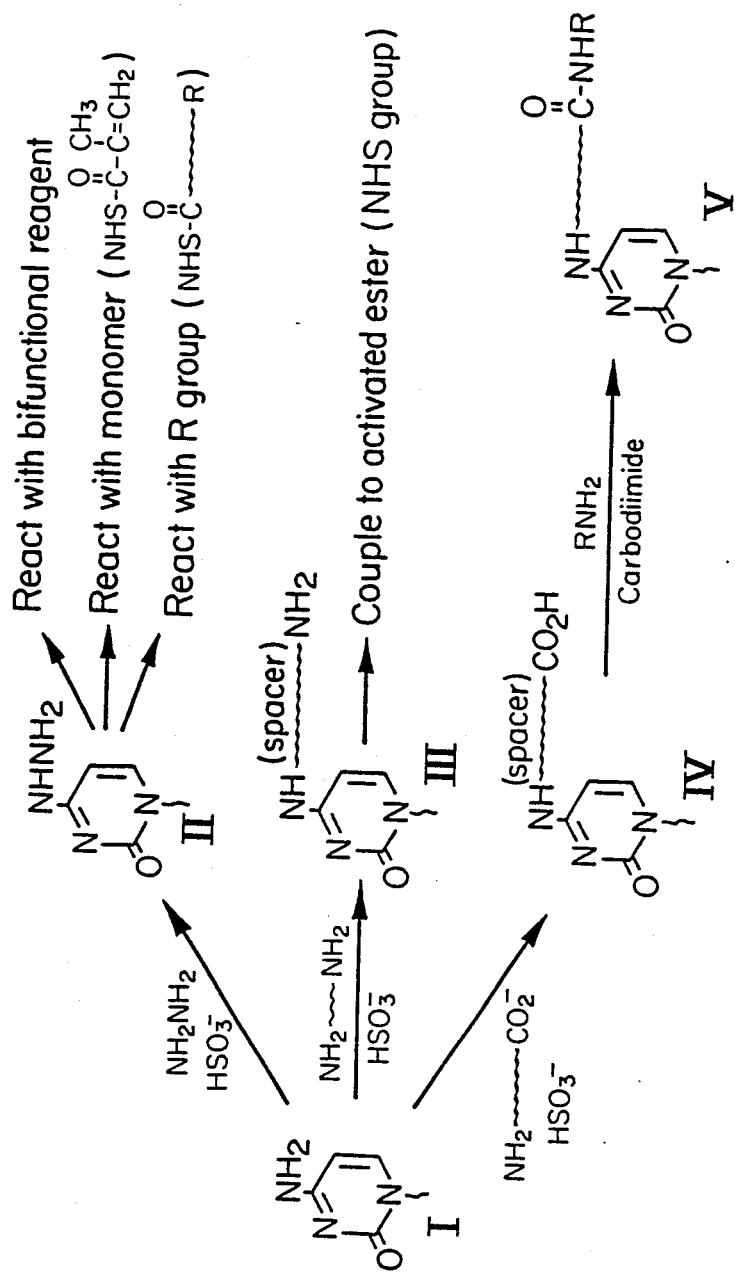
FIG. 3 depicts chemical reactions involving cytidine and hydrazine or primary amines in the presence of bisulfite.

As shown in FIG. 3, cytidine (I) can be readily modified in the presence of 2.5M hydrazine ($NH_2NH_2$) and 1M bisulfite ($HSO_3^-$) at pH 6-7 and 30° C. to form the 4-aminocytidine derivative (II) (Sverdlov et al., FEBS Lett. 62:212, 1976). An important feature of this reaction is that it is single-strand specific within polynucleotides. Using nearly the same conditions (1-5 M amine, 1M bisulfite, pH 6-7), the cytidine moiety also can be reacted with diamines to produce substituted cytidine derivatives (such as III) containing primary amines on spacer arms. Alternatively, the cytidine can be reacted with glycine or its analogs to produce cytidine derivatives such as (IV) with spacer arms connected to carboxyl functional groups. These carboxyl groups, in turn, can be coupled with a primary amine in the presence of carbodiimide to form derivatives such as (V) containing monomer, reporter, or other groups.

Figure 4:
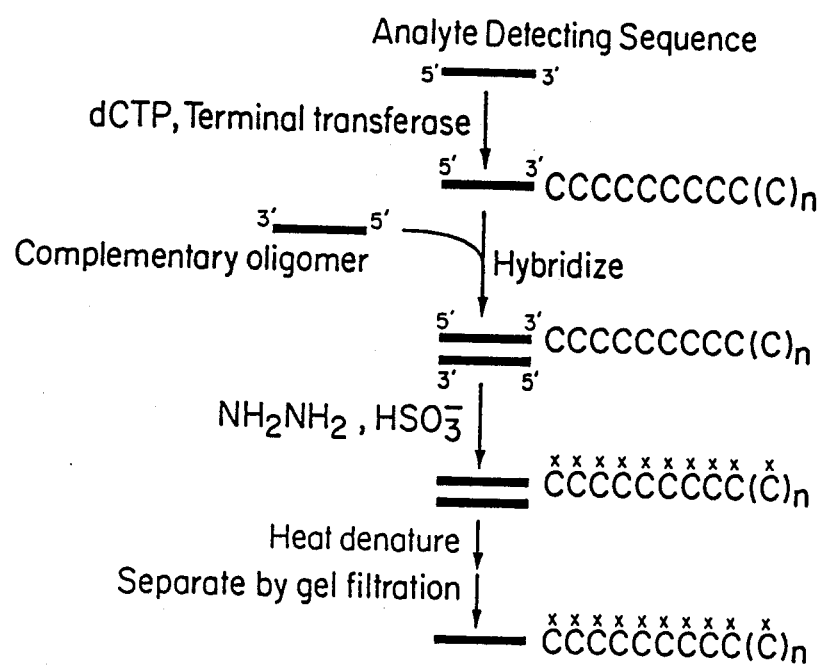
FIG. 4 depicts the single-strand specific conversion of cytidine residues to 4-aminocytidines by hydrazine and bisulfite.

The first reaction above can be exploited as follows. As shown in FIG. 4, an analyte detecting sequence, typically containing 20-30 nucleotides, is tailed with dCTP and terminal transferase. Probes typically containing attached sequences of 50 or more nucleotides are isolated and hybridized to a second DNA oligomer exactly complementary to the analyte detecting sequence. The resultant probe, which is now partially double-stranded, is treated with hydrazine and bisulfite such that only those portions of the probe which are single-stranded react. The derivative formed is N-amino-6-sulphonate-5,6-dehydrocytidine, which can be transformed into 4-aminocytidine (II in FIG. 3) by removal or dilution of the bisulfite or by raising the pH of the reaction medium. The material is desalted by ethanol precipitation, and then heat denatured and passed through a Sephadex G200 column to separate the tailed derivatized probe from the small complementary oligonucleotide. The probe now contains 4-aminocytidine residues predominantly in its attached sequence (since the cytidines within the probe itself were protected by virtue of their double-strandedness). The 4-amino group of this derivative is nucleophilic (Hayatsu et al., Nuc. Acids Res. Special Publication No. 5, s315, 1978) and can be used in the specific derivatizations shown in FIG. 3.

The advantage of the above procedure is that a probe can be extended by treatment with deoxycytidine 5'-triphosphate and terminal transferase under standardized conditions to yield well characterized poly(dC) attached sequence lengths. The chemical specificity of the derivatization reactions described then allows modification of only the attached sequence portion of the probe with, for example, monomer (e.g., reaction of 4-aminocytidine with the NHS-ester of methacrylate) or reporter groups (e.g., reaction of 4-aminocytidine with fluorescein isothiocyanate).

(3) C-5 Substituted Pyrimidines

Modified nucleotides in which the base moiety contains a charged group, such as a primary amine or carboxyl, usually are not acceptable to DNA synthetic enzymes. This is thought to be due to the proximity of the charged group to the enzyme's active site. To overcome this problem, the charged group can be separated from the pyrimidine nucleus by a spacer arm.

C-5 substituted pyrimidines can be synthesized by treating C-5 mercurated deoxyuridine 5'-triphosphate with a variety of olefins in the presence of a palladium catalyst (Bergstrom et al., J. Am. Chem. Soc. 98:1587, 1976; Bergstrom et al., J. Am. Chem. Soc. 100:8106, 1978; Langer et al., Proc. Natl. Acad. Sci. (USA) 78:6633, 1981). It is thought that the 5'-triphosphates of such compounds (for example, compound (I) in FIG. 5a or compound (VI) in FIG. 5b) can be used directly as substrates for terminal transferase. Following polymerization, the reactive nucleophilic amino groups on these modified bases can be coupled to a monomer. Prior to coupling to a reporter, however, it may be desirable to remove the exocyclic double bond by catalytic hydrogenation to yield, for example, compound (III) in FIG. 5a. The resultant derivatives then can be coupled directly with a reporter group to produce compound (IV) or (V).

In the event that compounds such as (I) or (III), or analogous compounds derived from compound (VI), are not acceptable substrates for the relevant enzyme, the charged amino group can be reversibly blocked. Once the compound is incorporated into RNA or DNA, the blocking group would be removed, and the nucleophilic amino group could be coupled to monomer or reporter.

(4) 5-Thiocytidine or 5-Thiouridine

A potentially useful reaction involves thiolation of deoxyuridine or deoxycytidine to form the thiol derivatives I and II, respectively, shown in FIG. 6(a) (Bardos et al., Nucleic Acid Chemistry, L. B. Townsend & R. S. Tipson eds., John Wiley and Sons, N.Y., 881, 1978). This reaction takes place under mild conditions within polynucleotides. Briefly, a probe (analyte detecting sequence tailed with poly(dU) or poly(dC)) is converted to the cetyltrimethylammonium salt, dried extensively, dissolved in methanol and treated with methyl hypobromite for 30 minutes at 0° C. Dry N,N-dimethylacetamide is added, the solution is flushed with nitrogen, and then freshly ground NaHS is added and mixed for 1-1.5 hours at 0° C. The polynucleotide is precipitated by the addition of sodium chloride, and subsequently purified by passage through a column of Sephadex G200. This procedure will introduce thiol groups into deoxycytidine or deoxyuridine (but not thymidine) residues located both in the analyte detecting sequence and in the tails (attached sequences). It is not expected that the presence of the thiolated derivatives in the analyte detecting sequence will interfere substantially with the specificity of base pairing.

Since the sulfur group is highly nucleophilic the thiolated derivatives (I) and (II) are of use for introducing a variety of side chains carrying, for example, monomer or reporter, into polynucleotides. For instance, a bifunctional reagent containing maleimide at one end and an NHS-ester at the other is commercially available. Treatment of a thiolated polynucleotide with this derivative allows the coupling of a spacer with an activated NHS-ester at one end. This NHS-ester could be used for the introduction of reporter or monomer groups in a subsequent step. The thiol group could also be reacted with iodoacetic acid (as shown in FIG. 6b) to introduce a carboxyl group for coupling to a primary amine-containing compound in the presence of a water soluble carbodiimide.

The same chemistry can be used to introduce thiol groups into deoxynucleoside 5'-triphosphates as well as polynucleotides. The resultant deoxy-5-thiouridine 5'-triphosphate or deoxy-5-thiocytidine 5'-triphosphate can then be used for the preparation of modified nucleotides containing, for example, carboxylic acid groups or primary amines separated from the pyrimidine by long spacer arms. This can be accomplished as shown in FIG. 5b, wherein the 5-thiol-containing nucleotide is reacted with iodoacetic acid, then coupled to a diamino compound in the presence of a carbodiimide to yield compound (IV). This derivative is expected to be a substrate for DNA synthetic enzymes, such as terminal transferase, or for RNA synthetic enzymes, such as polynucleotide phosphorylase where the appropriate ribonucleoside 5'-diphosphate has been synthesized. The derivative is tailed onto an analyte detecting sequence and coupled directly to an activated ester of methacrylic acid or to FITC. The primary amino group of compound (IV) can also be reversibly blocked, if necessary, to make it acceptable to the synthetic enzymes.

(5) Derivatization of a 3'-Terminal Ribonucleotide

An oligomer containing a ribonucleotide at its 3' end can be chemically modified with a primary amine containing a fluor or monomer as shown in FIG. 7(a). Treatment of the oligomer (I) with periodate oxidizes the 3' cis-glycol to produce the dialdehyde derivative (II). If a primary amine is introduced and the medium is kept at basic pH and at 0° C., a Schiff base is formed which can be reduced with sodium borohydride or sodium cyanoborohydride to produce the stable morpholinium derivative (III) (Khym, Biochemistry 2:344, 1963). This procedure has been used to introduce 1,5-diaminopentane directly into the 3' end of an RNA; the free primary amine produced was then treated with fluorescein isothiocyanate (FITC) to introduce a fluorescent reporter group (Broker et al., Nucl. Acids Res. 5:363, 1978). Alternatively, the primary amine could be reacted directly with the N-hydroxysuccinimide ester of methacrylic acid in order to introduce monomer.

Monomer or reporter groups could also be introduced directly into probes having structure (II). For instance, (II) could be treated with 2-aminoethylmethacrylate or a primary amine-containing fluorescein derivative at basic pH. Reduction with sodium cyanoborohydride would stabilize the Schiff base and allow the permanent incorporation of the monomer or reporter.

In practice, a ribonucleotide is introduced onto the end of a synthetic DNA oligomer as shown in FIG. 7(b). The oligomer is treated with terminal transferase and ribonucleoside 5'-triphosphate, to produce short tails containing one to four ribonucleotides. Treatment of the products of this reaction with base (0.3 N NaOH, 18 hours, 37° C.), followed by neutralization, and treatment with phosphatase will produce a DNA oligomer containing a single 3'-terminal ribonucleotide. This residue can be oxidized with periodate to produce the dialdehyde derivative, which can be treated first with the appropriate amine, and then with sodium cyanoborohydride for the stable incorporation of a reporter, monomer, or other group.

(6) Phosphoramidates

Figure 8B:
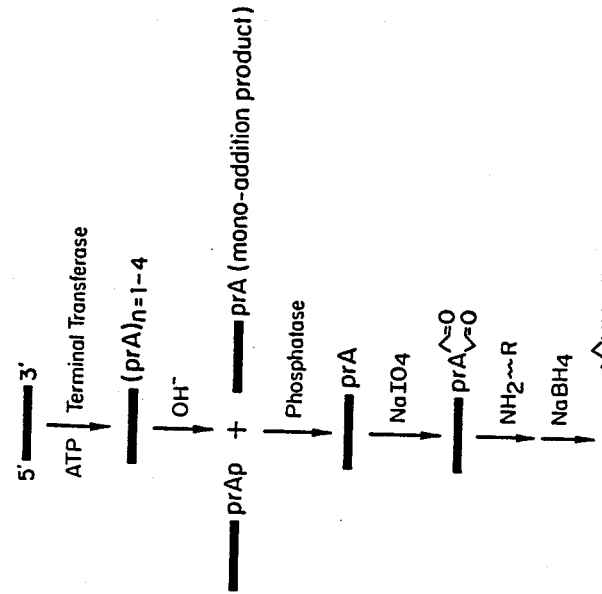
FIG. 8(b) depicts chemical reactions which can be utilized to introduce reporter, monomer, or other groups onto the free amine of phosphoramidate derivatives.
Figure 8A:
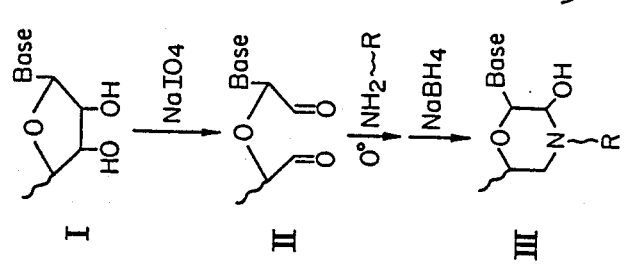
FIG. 8(a) depicts the conversion of a terminal phosphate of an oligonucleotide to a phosphoramidate.

When treated with a primary amine in the presence of diisopropylcarbodiimide in a mixture of water, dimethylformamide, and tert-butyl alcohol, the terminal phosphate of an oligonucleotide or polynucleotide can be converted to a phosphoramidate derivative (such as compound (I) in FIG. 8; Ralph et al., J. Am. Chem. Soc. 85:2002, 1963).

This reaction can be accomplished more conveniently in aqueous solution by treating an oligonucleotide containing a terminal phosphate with 0.5M primary amine and 0.1M 1-ethyl-3-(3-dimethylaminopropyl)-carbodiimide (EDC) in 0.1M 2-[N-morpholino]ethane sulfonic acid (MES) buffer, pH 6.0. A high yield of phosphoramidate occurs when the reaction mixture is rapidly evaporated to dryness several times at about 40° C., during which process the desired reaction is facilitated by concentration of the reagents.

These reactions can be used to add diamines such as 1,4-diaminobutane to form compound (II), as shown in FIG. 8(b). The derivative formed can then be reacted with fluorescein isothiocyanate to form compound (III) or with an activated ester of methacrylic acid to form compound (IV), for labeling with reporter or monomer groups, respectively. Alternatively, if the reporter or monomer contains a primary amino group, it can be condensed directly with the phosphate to form the phosphoramidate linkage.

(7) RNA Ligase-Catalyzed Addition of Reporter or Monomer Groups

One possibility for introduction of a monomer or reporter is to use a unique enzymatic addition property of RNA ligase. In the absence of ATP, treatment of an oligoribonucleotide with adenosine-5'pp-X in the presence of RNA ligase will result in the transfer of pX to the 3'-hydroxyl of the oligoribonucleotide to form a 3'-phosphodiester bond with concomitant release of adenosine 5'-phosphate, as shown in FIG. 9. This reaction has been used to produce oligoribonucleotides or polynucleotides with fluorescein or a primary amine at their 3' ends, having structures analagous to (I) and (II), respectively (Richardson et al., Nucl. Acids Res. 11:6167, 1983). The primary disadvantage of this method is that group X is attached to a ribose moiety and therefore is susceptible to alkaline hydrolysis or to scission with a ribonuclease. Another possibility is to use this ligase reaction for the direct addition of monomer to produce structure (III).

Oligonucleotides having a 3'-terminus corresponding to (II) can also be reacted with fluorescein isothiocyanate. In addition, (II) can be reacted directly with the N-hydroxysuccinimide ester of methacrylate in order to introduce monomer into the 3' end of the oligonucleotide.

In practice a DNA probe is converted to an efficient substrate for RNA ligase by adding one or more ribonucleotides to its 3' end. This is accomplished by treating the probe with a ribonucleoside 5'-triphosphate and terminal transferase to introduce one to four ribonucleotides as described above. The reaction products are then typically treated with alkali, neutralized, and treated with phosphatase to produce a DNA oligomer containing a single 3'-terminal ribonucleotide.

c. Synthesis of Class II Tailed Probes (Synthetic Labeling)

For purposes of illustration, the analyte detecting sequence is again assumed to be a short synthetic oligonucleotide. Tailing is carried out as described above using terminal transferase and derivatized deoxynucleoside 5'-triphosphates.

(1) C-5 Substituted Pyrimidines

Bergstrom et al. (J. Am. Chem. Soc. 100:8106, 1978), have described methods for the synthesis of C-5 substituted pyrimidine nucleosides by treating C-5 mercurated deoxyuridine with olefins in the presence of a palladium catalyst. As shown in FIG. 5, Ward has used this chemistry to synthesize 5-(3-amino)allyldeoxyuridine 5'-triphosphate (compound (I)) which is an intermediate in the synthesis of biotinylated-dUTP (Langer et al., Proc. Nat. Acad. Sci. (USA) 78:6633, 1981). Compound I is a convenient precursor to derivatives, containing either monomer or reporter groups, which can serve as substrates for DNA terminal transferase. For example, (I) can be reacted with the N-hydroxysuccinimide ester of methacrylate to form derivative (II) containing monomer, or (after hydrogenation over palladium) with fluorescein isothiocyanate to form (IV). Alternatively, (I) can be reacted (after hydrogenation) with a reporter on a spacer arm to form derivative (V). It should also be appreciated that spacer arms can be introduced using the precursor (VI) shown in FIG. 5(b).

(2) 5-Aminouridine 5'-Triphosphate

Figure 10:
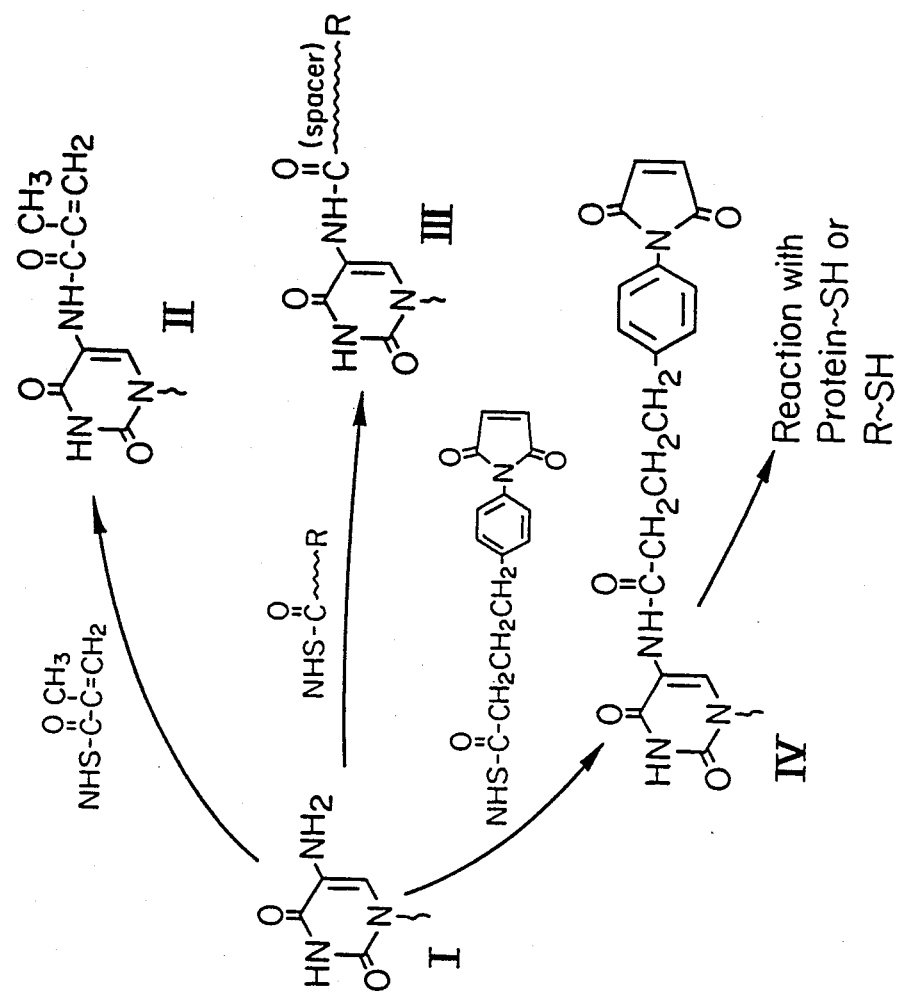
FIG. 10 depicts chemical reactions involving 5-aminouridine.

Another potentially useful nucleotide is the commercially available 5-aminouridine (Sigma Chemical Co., St. Louis, Mo.), shown in FIG. 10 (compound (I)). This molecule can be converted to the ribonucleoside 5'-diphosphate and derivatized such that the primary amine at the 5-position is coupled to produce a monomer-labeled nucleotide (II), a reporter-labeled nucleotide (III), or a nucleotide (IV) containing a reactive maleimide group. The derivatives produced are expected to be substrates for polynucleotide phosphorylase and therefore can be tailed directly onto DNA probes containing one or more 3'-terminal ribonucleotides.

(3) 5-Thiocytidine 5'-triphosphate and 5-Thiouridine 5'-triphosphate

Deoxycytidine 5'-triphosphate and deoxyuridine 5'-triphosphate can be converted to the corresponding 5-thiol derivatives as shown in FIG. 6(a). The resultant thiolated nucleotides can be reacted with sulfhydryl-specific reagents to which monomer or reporter groups have been attached. The labeled nucleotides are expected to be acceptable substrates for terminal transferase and thus can be tailed directly onto the analyte detecting sequence. The corresponding thiolated ribonucleoside 5'-diphosphate can also be utilized in polynucleotide phosphorylase-catalyzed tailing onto a DNA probe containing one or more 3'-terminal ribonucleotides (Ho et al., Nucl. Acids Res. 8:3175, 1980).

(4) Triester Synthesis

Reporter or monomer groups can be introduced into the probe during its chemical synthesis by the triester method. This can only be accomplished if the introduced group does not behave as a nucleophile during the formation of the triester in each coupling step. In one approach, a nucleotide containing an amine blocked with trifluoroacetic acid, or a carboxylic acid in the form of an ester could be incorporated during synthesis. Once synthesis is completed, the blocking group or ester can be removed, resulting in an amine or carboxylic acid which can be used for coupling to monomer or reporter groups. For example, 5-(3-amino)allyldeoxyuridine could be used as a core unit in the triester approach if the side chain primary amino group was suitably blocked. Following synthesis of the probe, this blocking group could be removed and the resultant amino group reacted with, for instance, the N-hydroxysuccinimide ester of methacrylic acid, or fluorescein isothiocyanate.

In some cases, it may be desirable to leave oligonucleotides in the triester form. Studies have indicated that the presence of ethyl groups in a triester lessens the ionic strength dependence of hybridization (Pless et al., Biochemistry 16:1239, 1977).

d. Synthesis of Class III Tailed Probes (Indirect Labeling)

One strategy for introducing reporter or monomer groups into probes is to tail the analyte detecting sequence with an "odd" base not normally found in prokaryotic or eukaryotic DNA or RNA. Antibody can be made to the "odd" base and labeled with a monomer or reporter. Binding of labeled antibody to "odd" bases in the probe will result in indirect labeling of the probe.

For example, analyte detecting sequences can be tailed readily with 5-bromodeoxyuridine 5'-triphosphate using terminal transferase. These tails can be specifically recognized by antibody to 5-bromodeoxyuridine (Gratzner, Science 218:474, 1982). Antibody can be labeled with a reporter group by methods well-known in the art or with a monomer, as described above. Upon binding of labeled antibody to the 5-bromodeoxyuridine tail, the probe becomes indirectly labeled.

Similarly, 5-(3-amino)allyldeoxyuridine 5'-triphosphate can be biotinylated, as described above, and tailed onto analyte detecting sequence. Avidin, a specific binding partner for biotin, can be labeled with monomer or reporter and bound to the biotinylated tail of the probe to provide an indirect label for that probe.

"Odd" bases can also be introduced during triester synthesis. For example, 5-bromodeoxyuridine has been introduced by this method into DNA fragments of about 20 nucleotides in length (Stawinski et al., Nucl. Acids Res. 4:353, 1977).

C-5 substituted pyrimidines containing blocked primary amines on spacer arms can also be introduced by the triester method. After synthesis has been completed, the substituted pyrimidine can be deblocked and derivatized, for example, by reaction with 2,4-dinitrofluorobenzene to yield an antigenic odd base.

It will be appreciated that indirect labeling can be accomplished by modifying the sugar moieties (e.g., by addition of 2'-amino or 2'-azido groups) or the phosphodiester bonds (e.g., by substituting phosphorothioate internucleotide linkages), as well as by modifying the bases themselves.

e. Synthesis of Probes in M13

Analyte detecting sequences greater than or equal to the size of synthetic oligonucleotides can be cloned and labeled in a suitable vector, such as M13. One possible advantage of cloning the analyte detecting sequence in M13 is that one has as many as 7,000 nucleotides (in M13) which can potentially be labeled. This affords a tremendous amplification of signal which can be especially important when the analyte is present in low concentration.

Messing and co-workers have constructed strains of M13 phage in which the lac promoter-operator region of E. coli has been inserted between genes IV and II (Messing et al., Proc. Natl. Acad. Sci. (USA) 74:3642, (1977); Gronenborn et al., Nature 272:375, 1978). The lac promoter-operator region which has been inserted, for example, in the mp 2 strain of M13, encodes the N-terminal 145 amino acid residues of the enzyme B-galactosidase.

There exist certain mutants of E. coli K12, for example, JM 101 and JM 103, which carry deletions in the B-galactosidase structural gene that result in enzyme lacking a portion of the N-terminal amino acid sequence. Transfection of these mutants with, for example, M13 mp 2 (which encodes the missing amino acids), results in complementation of the defective B-galactosidase, i.e., restoration of enzymatic activity. Complementation is conveniently monitored by growing the transfected cells on medium containing a chromogenic substrate for B-galactosidase, such as 5-bromo-4-chloro-3-indolyl-B-D-galactoside (Xgal), and an inducer of lac operon expression such as isopropyl thiogalactoside (IPTG). Cells which have been transformed will have active B-galactosidase and will form colored plaques (due to cleavage of Xgal) when grown on this medium. Non-transfectants will lack active B-galactosidase and will form colorless plaques (Malamy, Mol. Gen. Genet. 119:207, 1972).

Messing et al. (Nucleic Acids Res. 9:309, 1981) have also inserted into the lac region of M13 mp 2 a 17-base pair oligonucleotide which contains multiple restriction sites and thus functions as a multipurpose cloning site (MCS). The resultant M13 strain, designated mp 7, retains the ability to complement the JM 103 mutant. However, if foreign DNA is inserted into the MCS, this ability to complement is lost. Hence, it is possible to screen for M13 mp 7 transfectants containing DNA inserts by growing transfected JM 103 cells on chromogenic substrate/IPTG-containing medium and selecting the colorless plaques.

(1) Synthesis of Class I Probes (Post-Synthetic Labeling)

Strains of M13 phage such as mp 7, 8, and 9 are useful for cloning and labeling the probes of this invention. Briefly, an analyte detecting sequence is inserted into the double-stranded replicative form (RF) of M13 mp 7 at the MCS (this procedure is well-known in the art and is described, for example, by Messing, Meth. Enzymol. 101:20, 1983 and in *M13 mp 7 Cloning Manual*, Bethesda Research Laboratories (1980), P.O. Box 577, Gaithersburg, MD 20760). *E. coli* JM 103 cells are transfected with the resultant phage DNA and plated on agar containing IPTG and a chromogenic substrate. Colorless plaques will form wherever the cells were transfected by phage containing inserted analyte detecting sequence in their DNA. The colorless plaques are picked and the phage are grown up and purified by polyethylene glycol precipitation. The DNA is released from the purified phage and deproteinized by phenol extraction. The purified single-stranded DNA so obtained can now be labeled with monomer or reporter, for example, by derivatizing cytidine bases, as shown in FIGS. 3 and 4, or by derivatizing cytidine, as shown in FIG. 6. In generating class I probes care must be taken to protect the specific analyte detecting sequence from alterations which may impair its binding properties.

(2) Synthesis of Class II Probes (Synthetic Labeling)

Class II probes can also be synthesized in M13. Briefly, single-stranded DNA containing an inserted analyte detecting sequence is prepared as described above. Replication of the M13 sequences and incorporation of derivatized nucleotides is then initiated at a site 5' to the inserted sequence where a hybridization primer binds. The primer provides a 3'—OH for the addition of nucleotides by DNA polymerase I (Klenow fragment) and is commercially available, for example, from Bethesda Research Laboratories and New England Biolabs. Typically, one adjusts the conditions of replication so that much of the M13 sequence is copied, but the analyte detecting sequence is not, i.e., it remains single-stranded. Again, most of the chemistries cited above for class II (synthetic) labeling of tailed probes are appropriate for use in the M13 system.

(3) Synthesis of Class III Probes (Indirect Labeling)

Class III probes can be prepared in M13 by incorporating odd bases, such as 5-bromodeoxyuridine, or biotinylated bases into M13 sequences. Such probes are then indirectly labeled, for example, with labeled antibody to 5-bromodeoxyuridine or with labeled avidin, respectively.

Although the above discussion has been confined to cloning in M13, it will be appreciated that oligonucleotides or restriction fragments can be cloned in other vectors as well.

The following examples are provided by the way of illustration, rather than implying any limitation of the present invention. Example I illustrates a simultaneous sandwich immunoassay for human IgM which utilizes 2 monoclonal antibodies, one conjugated directly with acrylic acid and the other, with fluorescein isothiocyanate (FITC); separation is achieved by copolymerization with 2-hydroxyethylmethacrylate (HEMA) at room temperature using sodium bisulfite to initiate the reaction. Example II also illustrates a simultaneous sandwich immunoassay for human IgM; however, in this example monomer is conjugated to monoclonal antibody via a spacer arm and separation is achieved by copolymerization at 37° C. using TEMED and ammonium persulfate to initiate the reaction. Example III illustrates a nucleic acid hybridization assay for adenovirus in which the analyte detecting sequences themselves are derivatized to form phosphoramidates which are subsequently labeled, one with fluorescein isothiocyanate and the other, with the NHS-ester of methacrylic acid. Example IV illustrates a nucleic acid hybridization assay for adenovirus utilizing two probes, one prepared in M13 and indirectly labeled with p-acrylamidobenzoic acid and the other, prepared in pBR 322 and indirectly labeled with FITC. Example V illustrates an assay for detecting a specific interaction of a protein (p19) with a nucleic acid (Rous Sarcoma virus RNA).

EXAMPLE I

Simultaneous Sandwich Immunoassay for Human IgM

A: Synthesis of an Activated Acrylic Acid Monomer for Coupling to Antibody

A mixture containing N-hydroxysuccinimide (NHS) (4.6 g, 40 mmol) and acryloyl chloride (18 mL, 220 mmol) was refluxed with vigorous stirring for 3 hours in an anhydrous atmosphere and the reaction mixture, a homogeneous solution, was evaporated to a syrup. Distilled water (50 mL) was added to the syrup and the mixture was stirred for 30 minutes at 4° C. Upon addition of chloroform (50 mL), the mixture was separated into layers, and the organic layer was extracted successively with water (generally 5 times with 50 mL each time) until the pH of the water layer was approximately 5. The aqueous solutions so obtained were combined and extracted once with chloroform (50 mL); this chloroform solution and the chloroform solution from above were combined, dried over sodium sulfate, and evaporated to a syrup. Crystals, obtained by storing the syrup overnight at −20° C., were triturated with diethyl ether, and harvested by filtration.

Recrystallization from absolute ethanol yielded 2.0 g of the desired product. This compound was analyzed by mass spectrometry, infrared spectroscopy, NMR, liquid chromatography, and melting point, and proved to be the N-hydroxysuccinimide ester of acrylic acid. This reaction is shown as FIG. 11.

B: Preparation of a Monomer/Antibody Conjugate

Figure 11:
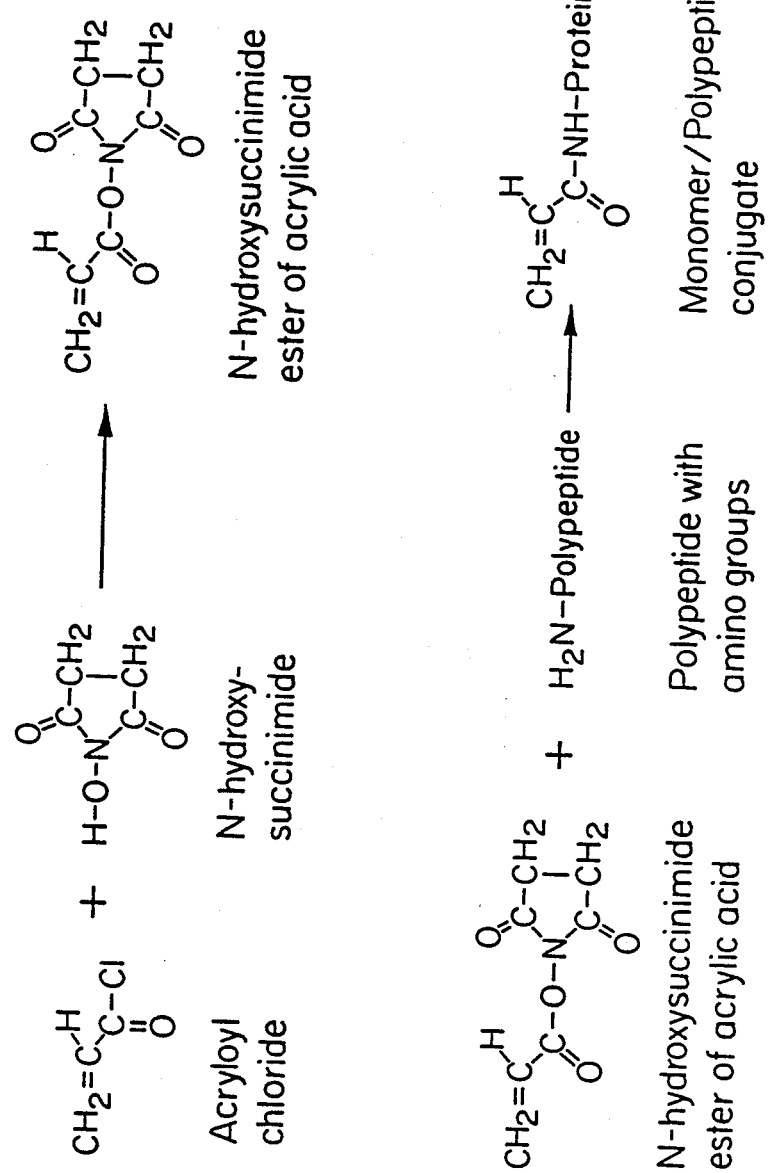
FIG. 11 depicts synthesis of an activated acrylic acid monomer and its conjugation to a polypeptide reactant of the present invention.

The N-hydroxysuccinimide ester of acrylic acid (NSA) was reacted with mouse monoclonal antibody (MAb) 2H1, which binds to human immunoglobulin kappa chains, as follows: 2.2 mg MAb in 0.29M sodium carbonate buffer, pH 9.3, was added to 20 micrograms of NSA in a total volume of 0.5 mL. The reaction mixture was incubated at 37° C. for one hour with constant stirring. Of this solution, 100 microliters was then taken for an analysis by reversed-phase high-performance liquid chromatography (RP-HPLC), which revealed the amount of free acrylic acid (arising from nonspecific hydrolysis of NSA) and remaining NSA in the reaction mix. The results are shown in Table 1. FIG. 11 shows the conjugation of NSA and MAb.

TABLE 1

RESULTS OF HPLC ANALYSIS OF MONOMER CONJUGATION REACTION MIXTURE

|  | Antibody | NSA (Activated monomer) | Acrylic Acid |
| --- | --- | --- | --- |
| Amount added, nanomoles | 14.5 | 116.0 | 0.0 |
| Amount detected in solution, nanomoles | not determined | 0.0 | 26.7 |

This analysis indicated that a net of 89 nanomoles of monomer was attached to the 14.5 nanomoles of MAb for a ratio of 6.2 monomer molecules per MAb.

To remove residual NSA and its hydrolysis products and for further characterization of the derivatized antibody, 200 microliters of the reaction mixture was chromatographed on a column of Sephadex G-25 (beads of dextran cross-linked with epichlorohydrin from Pharmacia Fine Chemicals AB, Uppsala, Sweden) in the same carbonate buffer to which bovine serum albumin, 0.1 mg/mL, was added to prevent nonspecific adsorption to the Sephadex G-25.

A sample of the monomer/antibody conjugate was then analyzed by isoelectric focusing. In this procedure, the polypeptide subunits of the proteins were separated according to their isoelectric point, or pH at which they had no net positive or negative charge. For this purpose, the heavy and light chains of the monomer/antibody conjugate were first dissociated in the presence of 3% (w/v) sodium dodecyl sulfate (SDS) and 5% (v/v) 2-mercaptoethanol and separated on the basis of molecular weight by electrophoresis in an SDS-polyacrylamide slab gel. The separated heavy and light chains were cut out from the gel and analyzed further by isoelectric focusing in a polyacrylamide slab gel according to their isoelectric point. Staining of the isoelectric focusing gel with dye (Coomassie Brilliant Blue R-250) provided a characteristic pattern of bands for each sample. Since both the heavy and light chains of antibodies are glycoproteins which contain intrinsic variations in their sialic acid content, each heavy and light chain can be separated by charge into a characteristic family of bands, with each band containing a polypeptide and differing amounts of sialic acid. As the reaction of the activated acrylic acid occurred primarily with amino functional groups on protein lysine residues, the addition of monomer to MAb would be expected to neutralize one positive charge on the protein subunit for each molecule of acrylic acid attached. This in turn would be expected to change the isoelectric point of the derivatized protein.

Figure 12:
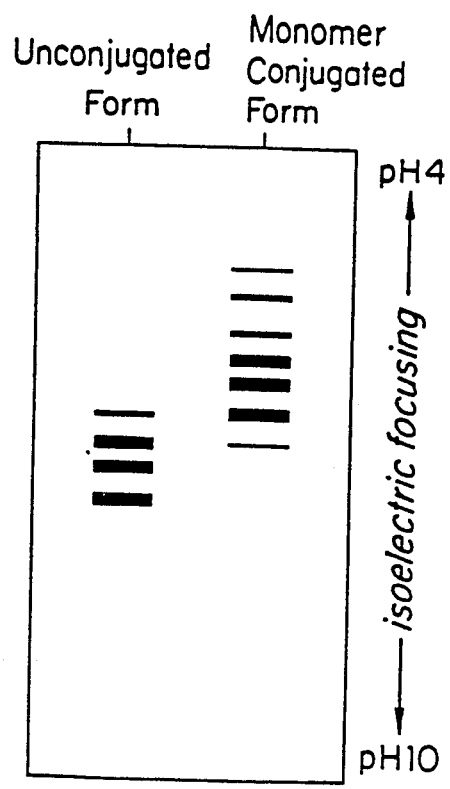
FIG. 12 is a diagrammatic representation of a polyacrylamide isoelectric focusing gel of the heavy chain of antibody 2H1 before and after conjugation with acrylic acid.

The results of the isoelectric focusing analysis indicated that each heavy chain was modified by the covalent attachment of approximately three acrylic monomers (FIG. 12). Analysis also indicated that the electrophoretic pattern of monomer-derivatized light chain was so close to the nonderivatized polypeptide pattern that essentially minimal conjugation of monomer to light chains had occurred. On this basis, it was estimated that six moles of acrylic acid monomer was conjugated to each mole of antibody (3 per heavy chain times 2 heavy chains per antibody), which was in agreement with the analysis by RP-HPLC.

C: Demonstration that the Monomer/Antibody Conjugate is Still Active

To show that the purified monomer/antibody conjugate was still active, it was tested in an enzyme linked immunosorbent assay (ELISA), and the results indicated no loss of antigen binding capacity. For this purpose, the antigen (human IgG, which contains kappa chains, like human IgM) was adsorbed to the surfaces of wells in a micro ELISA plate (96 wells). The wells were washed, residual nonspecific absorbing sites on the plastic surface were blocked with bovine serum albumin, and then incubated with serial dilutions of the antibodies (control unconjugated antibody and monomer/antibody conjugate). The plate was again washed, incubated with goat anti-mouse immunoglobulin conjugated to horseradish peroxidase (Tago, Inc., Burlingame, Calif. 94010), washed again, and incubated with the substrates for horseradish peroxidase, o-phenylenediamine and hydrogen peroxide. Dilute aqueous sulfuric acid was added to stop the reaction, the plates were assayed on a micro ELISA reader, and the optical densities of each dilution of monomer/antibody conjugate compared with that of the control unconjugated antibody. On a molar basis, the monomer/antibody conjugate demonstrated comparable activity to the unconjugated antibody.

D: Preparation of a Fluorescently Labeled Second Antibody

The final step in the assembly of the components of a simultaneous sandwich immunoassay system was the fluorescence labeling of a second monoclonal antibody (2C3, which reacts with the mu chain of human IgM) that bound to a different epitope of the antigen. Thus 2C3 did not block the binding of the first, monomer-conjugated antibody to the antigen. For this purpose, 60 micrograms (20 microliters of a 3.0 mg/mL solution in DMSO) of fluorescein isothiocyanate isomer II (FITC) was added to 1 milligram of antibody 2C3 in 0.125 mL of 0.27M carbonate buffer, pH 9.3. The mixture was incubated for 30 minutes at 37° C. and chromatographed on a column of Sephadex G-25 in phosphate buffered saline to which 0.5M NaCl and 0.1% NaN$_3$ had been added. This separated the fluorescein labeled antibody from any free FITC that remained in solution. The peak was collected in a volume of 0.25 mL and the fluorescein-to-protein (F/P) ratio, calculated from the absorbances at 280 nm and 495 nm using the equation F/P ratio=$3.1 \times A495/A280 - 0.31 \times A495$, was found to be 4.7. Using methods analogous to those in Example I(C), this fluorescently labeled antibody was found to be fully capable of binding to its antigen.

E: Polymerization of HEMA Monomer in a Buffered Saline Solution

Figure 13:
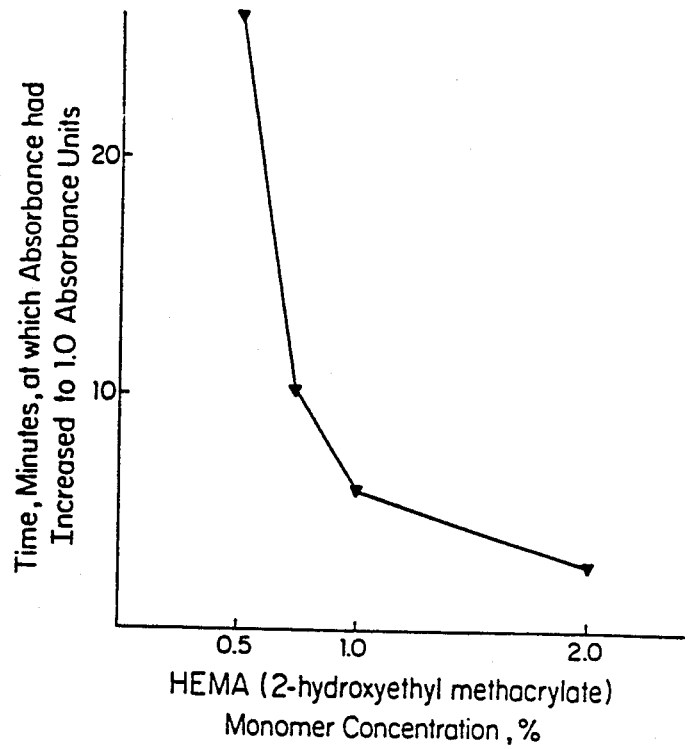
FIG. 13 depicts the effect of monomer (2-hydroxyethyl methacrylate, HEMA) concentration on the rate of formation of HEMA homopolymer particles.

Polymerization of 2-hydroxyethyl methacrylate (HEMA) in the presence of physiological compounds was carried out as follows: 2.73 mL of distilled water or phosphate-buffered saline, pH 7.4, was added to 0.24 mL of 25% (v/v) 2-hydroxyethyl methacrylate (HEMA, Aldrich Chemical Company). Water was added to a final volume of 2.97 mL, as necessary. After bubbling prepurified nitrogen through a Pasteur pipette into the bottom of the cuvet for at least five minutes, 30 microliters of 1M $Na_2S_2O_5$ was added and the precipitation of the resulting polymer was followed at 550 nm with a Beckman Model 26 spectrophotometer. FIG. 13 illustrates the dependence of the rate of precipitation on the concentration of monomer. From this data, a concentration of 2% was chosen.

Inclusion of fetal calf serum, up to 10% (v/v) or "Nonidet P-40," a nonionic detergent, available from Shell Chemical Co., at concentrations up to 10% (w/v), had no effect on the rate of formation of the polymer particles. Since fetal calf serum contains a variety of proteins and other physiological compounds, this indicates that many substances found in biological fluids will not inhibit formation of the polymer particles. Since nonionic detergents are commonly used in immunoassays to solubilize biological substances, these results indicate also that it will be possible to utilize detergents in polymerization-induced separation immunoassays without interference.

F: Demonstration of Antigen-Mediated Incorporation of Fluorescence into Polymer Particles A simultaneous sandwich immunoassay for human IgM was performed. In this method, the fluorescently labeled second antibody (2C3, 5 micrograms), the antigen (human IgM, 4.5 micrograms), and the monomer-conjugated antibody (2H1, 5 micrograms) were incubated together in a total volume of 90 μL for 30 minutes at 37° C., resulting in the formation of a ternary complex or sandwich. This complex contained both monomer and fluorescent label. Copolymerization (initiated with 10 L of sodium bisulfite, final concentration 20 mM) of this complex with additional nonderivatized monomer (HEMA) resulted in fluorescent, insoluble polymer particles (sample a).

For comparison, a control sample was prepared that was identical to the first except the antigen was omitted. This resulted in polymer particles that contained the monomer-conjugated antibody but not the fluorescently labeled antibody and that were non-fluorescent (sample b). To quantitatively compare the amounts of incorporation of fluorescence into the polymer particles from the two samples, they were subjected to quantitative flow analysis using a flow cytometer.

After the polymerization had proceeded for ten minutes, the suspension of polymer particles was diluted one-hundred-fold with PBS and then introduced into a flow cytometer (Becton Dickinson, FACS IV) equipped with an Argon ion laser light source. In this procedure, the suspended particles were carried single-file in a laminar stream of buffer. Interrogation of the particle stream with the laser beam generated light scatter each time a particle entered the laser pathway. The extent of the light scatter was a reflection of particle size and shape. The measurement of light scatter is used to electronically trigger a simultaneous measure of fluorescence emitted from the particle which was responsible for the light scatter signal. In this way, fluorescence specifically associated with polymer particles can be selectively measured.

Figure 14:
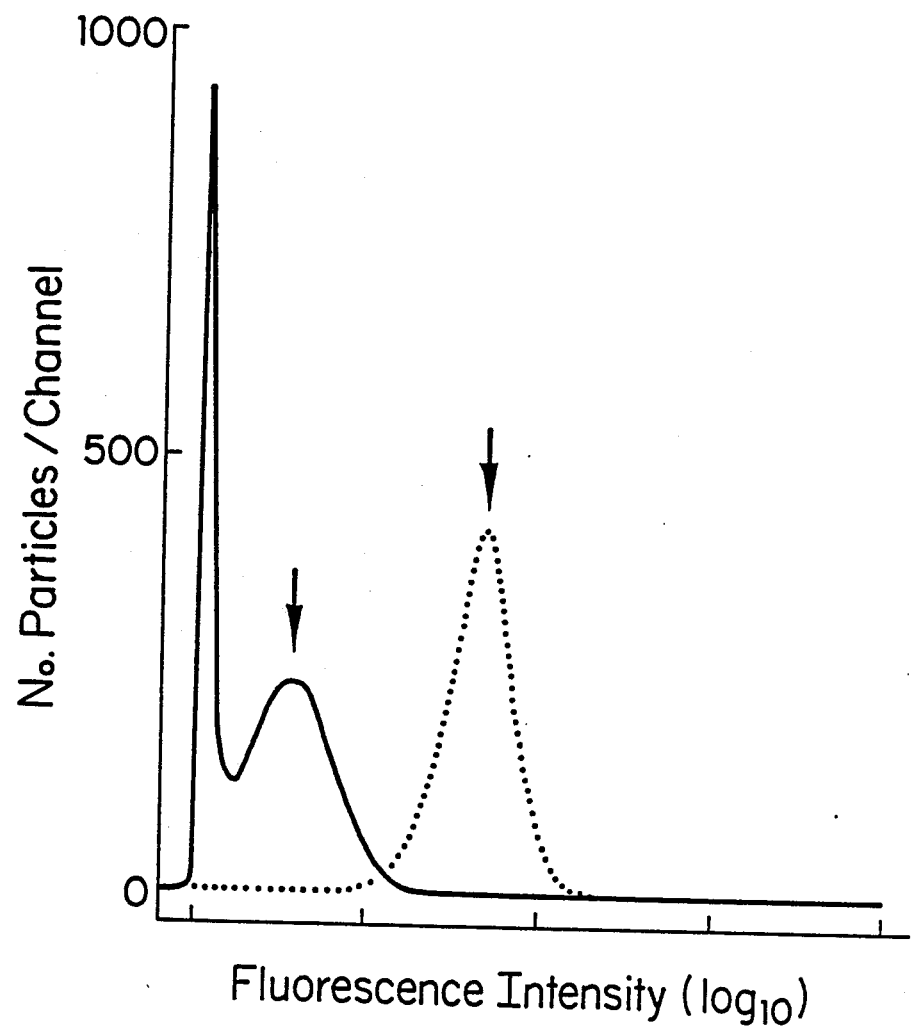
FIG. 14 depicts the antigen-mediated incorporation of fluorescein/antibody conjugate into polymer particles.
Figure 15:
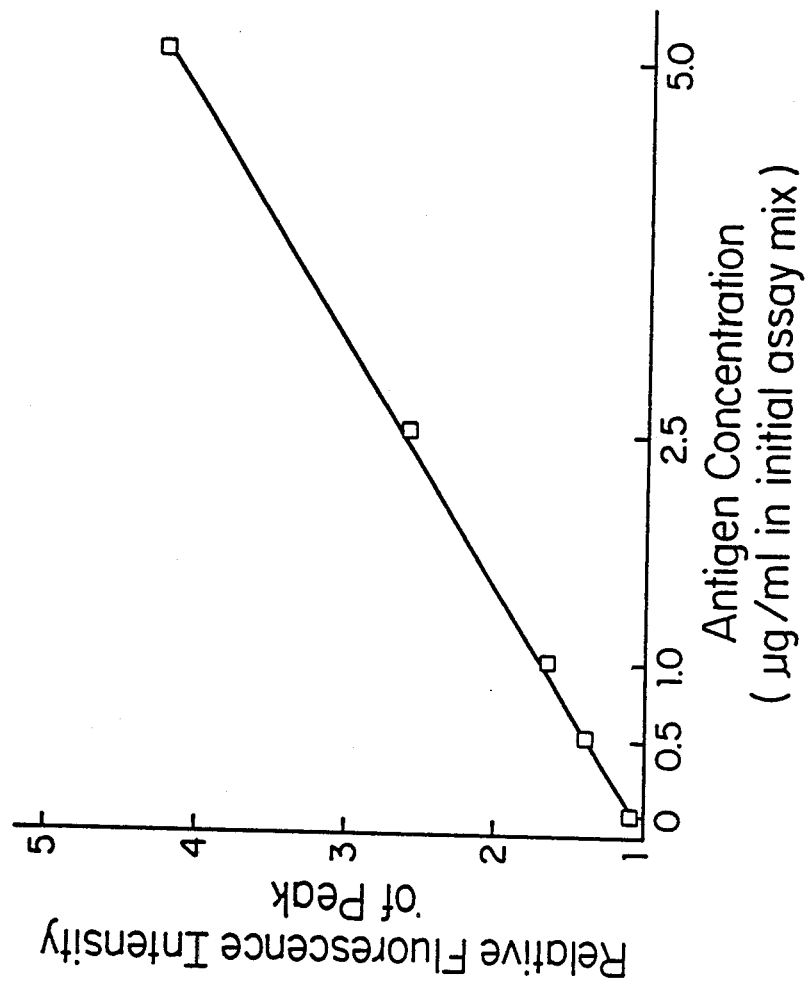
FIG. 15 is a diagrammatic representation of the relationship between fluorescence intensity and antigen concentration in one embodiment of the present invention.
Figure 17:
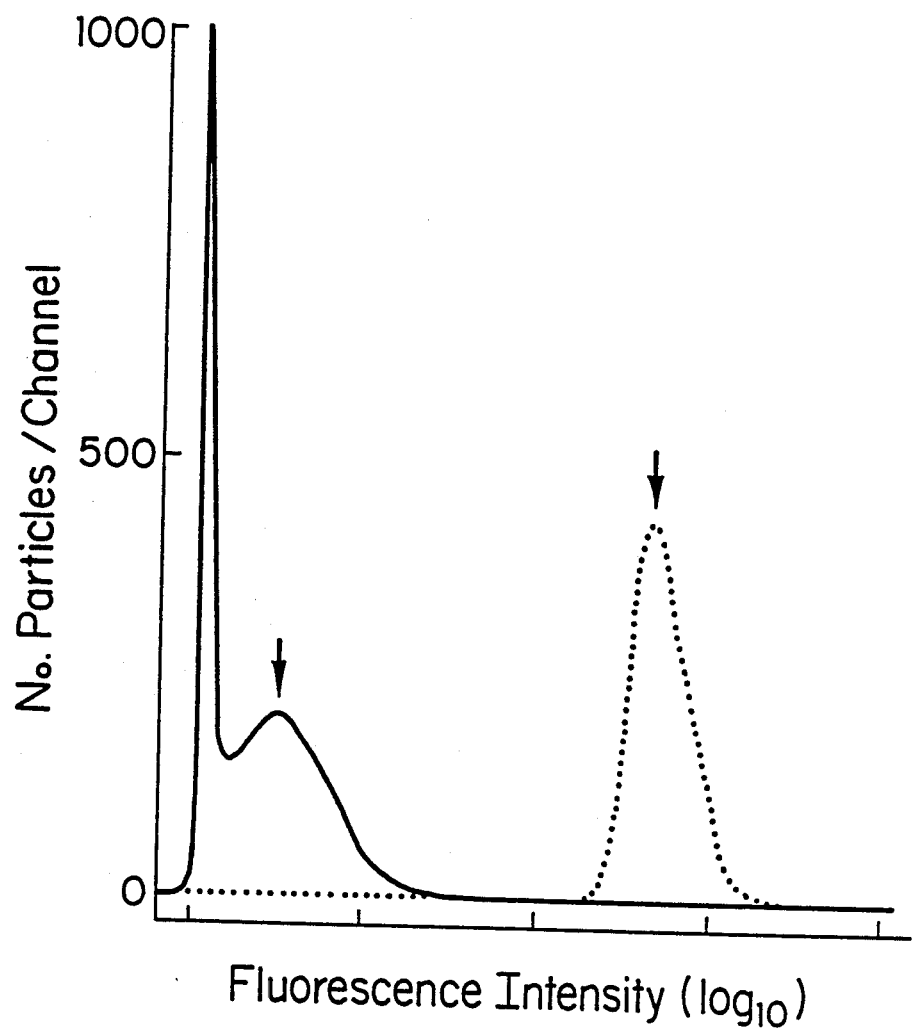
FIG. 17 depicts the combined effect of temperature, spacer arm and N,N,N',N'-tetramethylethylenediamine (TEMED)/persulfate initiation on the antigen-mediated incorporation of fluorescein/antibody conjugate into polymer particles.

The results are presented graphically in FIG. 14, which compares the fluorescence intensity of copolymer particles from sample a (dotted line) with the fluorescence intensity of copolymer particles from control sample b (solid line), from which the antigen was omitted. The fluorescence intensity of the copolymer particles formed in the presence of antigen (sample a) was shifted over 73 channels relative to the control. The fluorescence intensity scale (x axis) is logarithmic, and a shift of 73 channels corresponded to a 20-fold increase in fluorescence intensity. This increase in fluorescence intensity proved to be a linear function of the amount of antigen present in the sample. FIG. 15 is a plot of fluorescence intensity, on a linear scale, against the amount of antigen present in the sample, using 1 microgram of each antibody and otherwise the same conditions as used in FIG. 13.

EXAMPLE II

Simultaneous Sandwich Immunoassay for Human IgM

A simultaneous sandwich immunoassay for human IgM was performed as described in Example I above. However, in this example monomer was conjugated to antibody via a spacer arm, p-aminobenzoic acid. Copolymerization was initiated using TEMED and ammonium persulfate rather than sodium bisulfite, and copolymerization was conducted at 37° C. rather than at room temperature.

A: Synthesis of the N-Hydroxysuccinimidyl Ester of p-Acrylamidobenzoic Acid 0.66 g (7.3 mmoles) of acryloyl chloride was added to a solution of 2 g (14.3 mmoles) of p-aminobenzoic acid in 40 mL tetrahydrofuran (THF). A white precipitate consisting of p-aminobenzoic acid hydrochloride formed. The suspension was filtered and the filtrate was dried by vacuum evaporation to yield 1.1 g p-acrylamidobenzoic acid (reaction shown in FIG. 16a).

One gram (5.2 mmoles) of p-acrylamidobenzoic acid, 0.598 g (5.2 mmoles) of N-hydroxysuccinimide, and 1.07 g (5.2 mmoles) of dicyclohexylcarbodiimide were added to 25 mL THF at 4° C. The reaction was allowed to proceed for 20 hours, at which time a fluffy white precipitate had formed. The suspension was filtered and the filtrate was dried by vacuum evaporation. The resultant waxy pale green substance was triturated with diethyl ether and a pale yellow compound was recovered (reaction shown in FIG. 16b).

This compound was analyzed by mass spectrometry, infrared spectroscopy, NMR, and ultraviolet spectroscopy, and proved to be the N-hydroxysuccinimide ester of p-acrylamidobenzoic acid (NPBA).

B: Conjugation of NPBA to Mouse Monoclonal Antibody 2H1

The N-hydroxysuccinimide ester of acrylamidobenzoic acid (NPBA) was reacted with mouse monoclonal antibody 2H1 (reaction shown in FIG. 15c) as follows: 62.4 μL of a solution of 1mg/mL NPBA in DMSO was added to 1.33 mL (4.0 mg) 2H1 in 0.29M sodium carbonate buffer, pH 9.3. The reaction mixture was incubated at 37° C. for one hour with constant stirring.

To remove residual NPBA and its hydrolysis products and for further characterization of the derivatized antibody, the reaction mixture was chromatographed on a column of Sephadex ® G-25 which had been equilibrated in phosphate buffered saline (PBS), pH 7.4.

An aliquot of the resultant conjugate was analyzed by isoelectric focusing in polyacrylamide gel under non-reducing conditions. In this procedure the antibodies are separated according to their isoelectric point, or pH at which they have no net positive or negative charge. Staining of the isoelectric focusing gel with dye (Coomassie Brilliant Blue R-250) provided a characteristic pattern of bands for each sample. Comparison of NPBA-conjugated MAb with unconjugated (control) MAb indicated that an average of 4.2 monomers were bound per antibody for a coupling efficiency of 53%.

C: Preparation of a Fluorescently Labeled Second Antibody

Mouse MAb 2C3 labeled with FITC was prepared in Example I (D) above.

D: Demonstration of Antigen-Specific Incorporation of Fluorescence into Polymer Particles A simultaneous sandwich immunoassay for human IgM was performed. 3 micrograms each of fluorescein-conjugated MAb 2C3 and NPBA-conjugated MAb 2H1 were incubated together with 2 micrograms of human IgM in a final volume of 90 microliters of PBS for 30 minutes at 37° C. Copolymerization with HEMA was initiated by adding TEMED (5 $\mu$L, 40 mM final concentration) and then ammonium persulfate (5 $\mu$L, 5 mM final concentration). After ten minutes at 37° C., the reaction mixture was diluted 100-fold with PBS.

Figure 18:
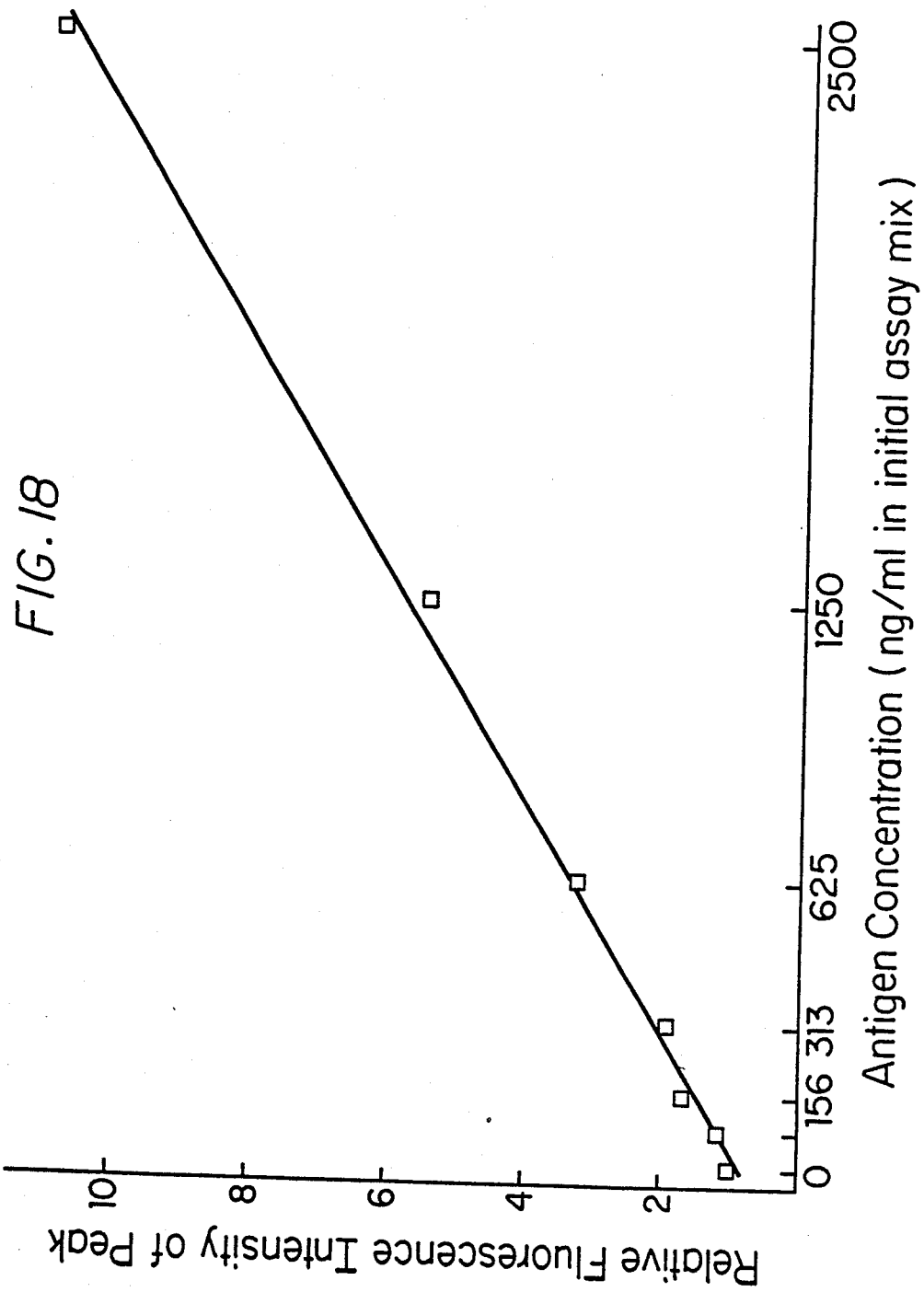
FIG. 18 is a diagrammatic representation of the relationship between fluorescence intensity and antigen concentration in one embodiment of the present invention.

The samples were then analyzed by flow cytometry as described in Example I (F) above. The results are shown in FIG. 16, where the dotted line represents the fluorescence intensity of copolymer particles formed in the presence of antigen, and the solid line represents the control, from which antigen was omitted. The fluorescence intensity of copolymer particles formed in the presence of antigen was shifted over 140 channels relative to the control. This corresponds to a 300-fold increase in fluorescence intensity over the control. This increase in fluorescence intensity also proved to be a linear function of the amount of antigen present in the sample, as illustrated in FIG. 18.

EXAMPLE III

Nucleic Acid Hybridizatin Assay for Adenovirus

A: Synthesis and Phosphorylation of Analyte Detecting Sequences

Synthetic oligonucleotides complementary to two sequences present in the adenovirus type 5 and 2 genome and separated by 41 nucleotides were synthesized by City of Hope, Beckman Research Institute, Duarte, Calif. The two sequences are shown below.

analyte detecting sequence 1: (5') GTGAGCTT-GAACCTGAAAGA (3')

analyte detecting sequence 2: (5') CGCGAC-GACGCGGCGGTTGA (3')

Each oligonucleotide is phosphorylated using T4 polynucleotide kinase as follows: To 20 $\mu$g of each oligonucleotide dissolved in 50 $\mu$L of 50 mM Tris HCl, pH 7.6/10 mM MgCl$_2$/5 mM DTT/0.1 mM spermidine/0.1 mM EDTA/1 mM ATP is added 3 $\mu$L (30 units) of T$_4$ polynucleotide kinase. The resultant mixture is incubated at 37° C. for 2 hours, after which 150 $\mu$L of water is added and the mixture is extracted twice with phenol (200 $\mu$L per extraction) and twice with ethyl ether (500 $\mu$L per extraction). The reaction products are fractionated by gel filtration on Bio-gel P-4 (0.5×20 cm column) equilibrated in 25 mM ammonium bicarbonate, pH 8.0. The phosphorylated oligomer, found in the excluded volume, is concentrated to dryness and redissolved in water and again concentrated, for a total of three cycles.

In order to be able to follow the derivatization, a small amount of each oligonucleotide (0.1 $\mu$g) is phosphorylated with [$\gamma$-32p] ATP (2900 Ci/mmole). Approximately 1000 cps of radiolabeled oligonucleotide is present in all subsequent steps, allowing the derivatization to be followed by autoradiography.

B: Synthesis of Class I Labeled Probes

5'-Phosphoramidate derivatives of the analyte detecting sequences are prepared as described below. Ten-twenty ug of each analyte detecting sequence is separately dissolved in 25 $\mu$L of 2M 1,4-diaminobutane and 5 $\mu$L of 1M MES (2-[N-morpholino]ethane sulfonic acid) buffer (pH6.0), followed by mixing with 25 $\mu$l of freshly prepared 0.2M 1-ethyl-3-(3-dimethylamino-propyl)-carbodiimide (EDC).

To facilitate the formation of the phosphoramidate derivative, the mixture is placed in a 10 mL glass tube and taken to dryness in vacuo at 40°–45° C. using a Buchi rotary evaporator. The material is redissolved in 50–100 $\mu$L of water and again taken to dryness; this cycle is repeated a total of three times. Alternatively, the mixture can be spotted on a 1 cm$^2$ sheet of Whatman 3MM filter paper and dried with a heat gun or hair dryer. After drying, a 50–100 $\mu$L aliquot of water is spotted on the paper and the drying step is repeated for a total of three times. The derivatized oligonucleotide is eluted from the paper in water and concentrated to dryness. The yield of the phosphoramidate derivatization by either of these methods is typically greater than 80%.

After the final evaporation by either of the above methods, the DNA is dissolved in 250 $\mu$L of 0.3M sodium acetate, 750 $\mu$L of ethanol is added, and the mixture is chilled at $-70$° C. for at least 15 minutes. The DNA is then centrifuged at 12,000 × g for five minutes at 4° C. and the supernatant discarded. The pellet is washed once with 1.5 mL of ethanol and dried in vacuo for 5 minutes.

The DNA is dissolved in 30 $\mu$L of 25mM Tris borate (pH 8.3)/5M urea, containing 0.025% each of bromphenol blue (BPB) and xylene cyanol (XC), heated to 90° C. for one minute, and electrophoresed on a 20% polyacrylamide slab gel (30:1 crosslinked) containing 50 mM Trisborate buffer (pH8.3) and 7M urea. The electrophoresis is terminated when the BP has migrated 40 cm from the origin. The position of the analyte detecting sequence in the gel is determined by autoradiography.

The region of the gel containing the derivatized analyte detecting sequence is excised and then crushed to a paste (Maxam et al., Meth. Enzymol. 65:499, 1980). To the paste is added 0.6 mL of 0.5M ammonium acetate/10 mM magnesium acetate/1 mM EDTA/0.1% SDS (elution buffer) and the mixture is incubated for ten hours at 37° C. The gel fragments are filtered through siliconized glass wool into a 10×75 mm siliconized glass tube. The paste is washed with 200 μL of elution buffer which also is filtered through the glass wool. The filtrates are combined and ethanol precipitated. The supernatant is discarded and the pellet is dissolved in 300 μL of 0.3M sodium acetate and transferred to a 1.5 mL siliconized Eppendorf tube. The mixture is again precipitated with ethanol, the pellet is washed once with ethanol and dried in vacuo for 15 minutes, dissolved in water, and stored at −20° C. The resultant analyte detecting sequence now contains a free amino group which can be derivatized, as described below, with either monomer or reporter.

The phosphoramidate derivative of analyte detecting sequence 1 (1–50 μg) is dissolved in 200 μL of 0.2M sodium carbonate buffer, pH 9.3. To this is added 5 μL of FITC (3 mg/mL in DMSO, freshly prepared). The mixture is incubated at 37° C. for 30 minutes, after which 20 μL of 1M glycine, pH 9.3 is added. The mixture is applied to a Sephadex G-25 column (0.7×20 cm) and eluted with 25 mM ammonium bicarbonate, pH 8.0. The peak fractions corresponding to fluoresceinated analyte detecting sequence are pooled and evaporated to dryness in a 1.5 mL siliconized Eppendorf tube. Greater than 90% of the analyte detecting sequence is expected to be fluoresceinated under these conditions.

The phosphoramidate derivative of analyte detecting sequence 2 is labeled with the NHS-ester of acrylic acid (NSA) prepared as described in Example I.A above. Briefly, 1–100 μg of the phosphoramidate derivative is dissolved in 200 μL of 0.29M sodium carbonate buffer, pH 9.3 and to this is added 20 μg of NSA. The solution is incubated at 37° C. for one hour with stirring, after which 20 μL of 0.5M glycine, pH 9.3 is added to stop the reaction. The solution is then mixed, first with 80 μL water/30 μL 3M sodium acetate and then with 1 mL of ethanol, followed by chilling at −70° C. for at least 15 minutes. The solution is then centrifuged at 12,000 ×g for 5 minutes at 4° C., the supernatant is discarded and the pellet is dissolved in 300 μl of 0.3M sodium acetate, and again ethanol precipitated. The recovered pellet is washed with ethanol, dried in vacuo, dissolved in water, and stored at −20° C. The resultant analyte detecting sequence is now labeled with monomer.

C: Demonstration of Incorporation of Reporter/Probe and Monomer/Probe into Polymer in Presence of Adenovirus DNA Purified adenovirus DNA prepared from HeLa cells infected with Ad-2 virus is obtained from Bethesda Research Laboratories, Inc. (Gaithersburg, Md.). This DNA (25 μg) is fragmented by treatment with 25 units of AluI restriction endonuclease in 100 μL 25 mM Tris-HCl, pH 7.5, 50 mM NaCl, 5 mM $MgCl_2$, 1 mM dithiothreitol for eight hours at 37° C. Water (125 μL), 3M sodium acetate (25 μL) and redistilled phenol (250 μL) is added and the mixture is vortexed and then centrifuged for several seconds at 12,000× g. The phenol (bottom layer) is removed with a capillary and the phenol extraction is repeated. Following removal of the phenol, 750 μL of ethanol is added and the solution is mixed, chilled for five minutes, and centrifuged at 12,000× g at 4° C. for five minutes. The supernatant is discarded and the pellet is washed with 1.5 mL of ethanol, dried in vacuo for several minutes, dissolved in 100 μL $H_2O$, and stored at −20° C.

An aliquot of the resultant restriction fragments (1–10 μg) are dissolved in 50 μL of 10 mM Tris-HCl, pH 8, heated for two minutes at 100° C. to denature duplexes, and then chilled rapidly in ice water. To this mixture is added 50 ng of fluoresceinated analyte detecting sequence 1, and 50 ng of monomerized analyte detecting sequence 2 in 50 μL of 12X NET buffer (1X NET is 0.15M NaCl/0.03M Tris-HCl, pH 8.0/1 mM EDTA). The assay mixture is incubated at 50° C. for six to twelve hours in a tightly sealed siliconized 1.5 mL Eppendorf tube. Afterwards the mixture is cooled to room temperature and made 1% in 2-hydroxyethylmethacrylate (HEMA). Following mixing, 5 μL of 0.8M TEMED in 0.1M sodium borate, pH 7, is added, followed immediately by 5 μL of 0.1M ammonium persulfate. The solution again is mixed rapidly and allowed to copolymerize at 37° C. for ten minutes. The solution is diluted with 1 mL of $H_2O$, vortexed frequently over a period of 15 minutes, and then analyzed by fluorescence microscopy or by quantitative flow analysis with the fluorescence-activated cell sorter to demonstrate the incorporation of fluorescence into polymer particles. A control reaction is run in parallel in which the adenoviral DNA fragments are replaced by salmon sperm DNA. Under these conditions, substantially less fluorescence is incorporated into the polymer. Similarly, when the monomer/probe conjugate is omitted from the reaction, there is substantially less fluorescence incorporation.

EXAMPLE IV

Nucleic Acid Hybridization Assay for Adenovirus

A nucleic acid hybridization assay for the detection of Adenovirus type 2 (Ad-2) is described which utilizes two restriction fragments as probes, one cloned in phage M13 and one cloned in plasmid pBR322, the former indirectly labeled with p-acrylamidobenzoic acid and the latter indirectly labeled with fluorescein.

A: Cloning Bam HI Fraqments of Ad-2 in pBR 322

Ad-2 DNA purified from virus-infected HeLa cells is obtained from Bethesda Research Laboratories, Inc. (Gaithersburg, Md.). This DNA (4 μg) is cleaved with Bam HI restriction endonuclease by incubating the DNA with 4–10 units of enzyme in 50 mM NaCl/10 mM Tris-HCl, pH 7.5/1 mM dithiothreitol/10 mM $MgCl_2$ at 37° C. for approximately 8 hours. An aliquot of the resultant digest is subjected to electrophoretic analysis to ascertain that digestion is complete. The remainder of the digest is then phenol extracted and ethanol precipitated as described above in Example III C.

Plasmid pBR322 is similarly cleaved with Bam HI, then treated with alkaline phosphatase to prevent reannealing of the cut ends. Briefly, 0.5 units of calf intestinal alkaline phosphatase is added to 1.5 μg of Bam HI cleaved plasmid DNA in a total volume of 50 μL of 0.01 M Tris, pH 9.5/0.001 M spermine/0.1 mM EDTA. The mixture is incubated at 37° C. for 30 minutes, then at 65°–70° C. for an additional 60 minutes. The mixture is then diluted with 0.02 M Tris HCl, pH 7.5/0.02 M NaCl/0.001 M EDTA to achieve a final concentration of 10 ng/μL.

The Bam HI fragments of Ad-2 DNA are then inserted into the Bam HI-cleaved, phosphatase-treated pBR322 DNA at a molar ratio between 10 and 50:1. Briefly, 10–40 ng of the cleaved plasmid DNA and 4 μg of the cleaved Ad-2 DNA are mixed with 2 μL of 10X buffer (0.1 M Tris, pH 9.5/0.01 M spermine/0.001 M EDTA), 2 μL of 1 mM rATP, and 3–5 units of DNA ligase (Bethesda Research Labs, Gaithersburg, Md.) in a final volume of 20 μL. The mixture is incubated at 16°–25° C. for approximately 16 hours, and the resultant ligated DNA is used to transform competent *E. coli* strain RRI cells by the calcium chloride method. Ampicillin-resistant colonies are picked and replica-plated on Luria broth agar containing either ampicillin (100 μg/mL) or tetracycline (15 μg/mL), as described in Maniatis et al. (Molecular Cloning: A Laboratory Manual, N.Y.: Cold Spring Harbor, 1982). These colonies are used to inoculate 2–3 mL broth cultures from which crude plasmid DNA is prepared, again as described by Maniatis. Separate clones containing Bam HI fragments C and D of Ad-2 DNA are identified by electrophoresis of Bam HI-cleaved recombinant plasmid DNA in a 0.7% agarose gel, followed by Southern blotting and hybridization to $^{32}$P-labeled, nick translated Ad-2 DNA (see R. W. Davis et al., eds. A Manual for Genetic Enqineering: Advanced Bacterial Genetics, New York: Cold Spring Harbor, 1980). Broth cultures are separately inoculated with a fragment C-containing clone and a fragment D-containing clone. From these cultures, large quantities of DNA are purified. Fragment D-containing probe is subsequently biotinylated and indirectly labeled with reporter. Fragment C is cleaved with a second restriction endonuclease and the resultant fragment is cloned in M13, labeled with BUdR, and indirectly labeled with monomer.

B: Indirect Labeling of a First Probe with Reporter pBR322 DNA containing the Bam HI-D fragment of Ad-2 (29.0–42.0 map units) is labeled by nick translation using biotinylated dUTP. Briefly, the following reagents are mixed on ice: 10 μL 0.5M Tris HCl, pH 7.5/50 mM MgCl$_2$; 10 μL nucleoside triphosphates (0.3 mM dATP, 0.3 mM dGTP, 0.3 mM dCTP in 50 mM Tris HCl, pH 7.5); 10 μL biotinylated dUTP (Enzo Biochem, New York, N.Y.), 0.3 mM in 50 mM Tris HCl, pH 7.5; 2 μg of pBR322 DNA containing the D fragment of Ad-2; 8 μL of DNAse I (0.1 g/mL in 10 mM Tris HCl, pH 7.5/0.1% BSA); and 8 μL of *E. coli* DNA polymerase I (3 units/μL in 0.1M sodium phosphate, pH 7.2/50% glycerol/1 mM DTT). To follow incorporation, 24 μL of 3H-ATP (0.25 μCi/μL in 50% aqueous ethanol) is dessicated in the tube to which the above reagents are added. The final volume is adjusted to 100 μL with distilled water and the reaction is allowed to proceed for 2 hours at 14°–15° C. After 2 hours, the reaction is stopped by adding 10 μL of 0.2M EDTA and incubating the resultant mixture at 65° C. for 10 minutes. The percent incorporation of biotinylated dUTP is typically 20–40%. Nick translated, biotinylated probe is purified by qel filtration on Sephadex G50 equilibrated in 10 mM Tris HCl, pH 7.5/1 mM EDTA.

The biotinylated probe so obtained is indirectly labeled after hybridization, by incubating with a goat anti-biotin antibody, followed by FITC-conjugated rabbit anti-goat IgG antibody (available, for example, from Enzo Biochem, New York, N.Y.).

C: Indirect Labeling of a Second Probe with Monomer

Fragment C of Ad-2 DNA (42.0–59.5 map units) is cleaved (1 μg) with the restriction endonuclease Bgl II (2–10 units) in 10 mM Tris HCl, pH 7.5/10 mM MgCl$_2$/1 mM dithiothreithol at 37° C. for approximately 5 hours. Then, 2–10 units of Bam HI is added and the NaCl concentration in the reaction is raised to 50 mM. The mixture is incubated at 37° C. for an additional 3 hours. An aliquot of the diqest is analyzed electrophoretically on a 1.0% agarose gel to ascertain that the digestion is complete. The remainder of the digest is subjected to preparative electrophoresis on a 1.0% agarose gel. A portion of the gel is stained with ethidium bromide and the fragment of interest, which maps between 42.0 and 45.3 map units, is identified by its relative mobility. This region is excised from the unstained gel. The fragment is electroeluted in 1X TBE buffer (0.089 M Tris-borate, pH 8.0/0.089M boric acid/0.002 M EDTA). The eluted DNA is purified by passing the eluate over an Elutip-d ™ column (Schleicher and Schuell Inc., Keene, N.H.) and eluting with 2–3 mL of 1.0 M NaCl/20 mM Tris HCl, pH 7.4/1 mM EDTA. Alternatively, the eluted DNA can be purified by high salt elution from DEAE cellulose (Whatman Ltd.). The recovered DNA is phenol extracted, ethanol precipitated and diluted to a concentration of approximately 12.5 ng/μL.

This DNA is now cloned into the replicative form (RF) of M13 as follows: The M13 RF is cleaved with Bam HI (10–25 units per 5 μg RF for 1.5–5 hours at 37° C.), phenol extracted, ethanol precipitated, and then sedimented in a velocity gradient (10% to 30% sucrose in 0.1 M Tris/0.1M NaCl/0.005M EDTA) in an SW 50.1 rotor at 50,000 rpm for three hours. An aliquot of the endonuclease-cleaved DNA is electrophoresed in a 1.0% agarose gel to ascertain that the digestion is complete. The remainder of the cleaved DNA is then treated with alkaline phosphatase to prevent reannealing of the cut ends as described in Example IV A.

The Bam/Bgl Ad-2 fragment (42.0–45.3 map units) is now inserted into the Bam HI cleaved, phosphatase-treated M13 DNA at a molar ratio of between 10–30:1. Briefly, 50 ng (5 μL) of the cleaved vector and 125 ng (in 10 μL) of purified Bam/Bgl Ad-2 fragment are mixed with 2 μL of 10X buffer (0.1M Tris, pH 9.5/0.01M spermine/0.001M EDTA), 2 μL of 1 mM rATP, and 2–10 units of DNA ligase (Bethesda Research Labs, Gaithersburg, Md.) in a final volume of 20 μL. The resultant mixture is incubated at 16°–25° C. for 16 hours.

Competent JM 103 cells (0.3 mL) are transfected with 2–5 ng of ligated M13 DNA containing the Ad-2 Bam/Bgl fragment. After overnight growth on YT plates containing IPTG and Xgal, the colorless (recombinant) plaques are selectively harvested and used to infect cultures of exponentially growing JM103 cells (2 mL). Virus is purified from the cultures after overnight growth by polyethylene glycol precipitation and their DNA is purified by phenol extraction and ethanol precipitation. The presence of the Bam/Bgl Ad-2 fragment in the purified DNAs is confirmed by electrophoresis of the DNA in agarose, followed by Southern blotting and hybridization with radiolabeled adenovirus. Those cultures which are confirmed as containing Ad-2 DNA are then expanded by infection of JM 103 cells (1 plaque/2 mL JM 103 cells, O.D. 660=0.3). Eight-12 hours later, the phage are purified by polyethylene glycol precipitation and their DNA is purified by phenol extraction and ethanol precipitation. The identity of the Ad-2 fragment in the M13 clones is confirmed by electrophoresing Ad-2 DNA cleaved with Bam HI, Bgl II, and both, followed by Southern blotting with radiolabeled DNA purified from the clones of interest.

5-Bromo-2'-deoxyuridine is incorporated into the probe as follows: Briefly, 6 μL of M13 DNA containing the fragment of interest (500 ng) is combined with 4 μL of hybridization probe primer (5 ng/μL in 7 mM Tris HCl, pH 7.5/7 mM MgCl$_2$/50 mM NaCl) plus 3 μL of 70 mM Tris HCl, pH 7.5/70 mM MgCl$_2$/0.5 M NaCl and 5 μL of distilled H$_2$O. The hybridization probe primer is pretreated by boiling for 2 minutes, then chilling immediately on ice before addition to the above reaction. The mixture is incubated at 65° C. for ten minutes in a sealed tube. The tube is then cooled slowly to room temperature (about 30 minutes), after which 2 μL of a mixture of dGTP, dCTP, dATP, and 5-bromo-2'-deoxyuridine 5'-triphosphate (0.5 mM each in 10 mM Tris, pH 7.5) are added. 1 μL of the Klenow fragment of DNA polymerase I (6 units/μL) is added and the mixture is incubated at room temperature for one hour. One μL of 0.5M EDTA is added to the mixture and the probe is separated from unincorporated nucleotides by gel filtration.

The probe is indirectly labeled, after hybridization, with a monomer-conjugated mouse monoclonal antibody reactive with bromodeoxyuridine. The antibody is prepared as described by Gratzner (Science 28:474, 1982) and is conjugated to monomer via a spacer arm as described in Example II above.

D: Hybridization Assay for Adenovirus 2.0 μg Ad-2 DNA is fragmented enzymatically with 2-10 units Bgl II restriction endonuclease in 10 mM Tris HCl, pH 7.5/10 mM MgCl$_2$/1 mM dithiothreitol at 37° C. for approximately 5 hours. An aliquot of the digest is analyzed electrophoretically to ascertain that digestion is complete. The remainder of the digest is then phenol extracted and ethanol precipitated.

The fragmented Ad-2 DNA is resuspended in 50 μL of 4X SSC (1X SSC=0.15M NaCl/0.015M sodium citrate, pH 7.6). Approximately 400 ng (10 μL) of this solution is added to 1.0 μg of biotinylated probe along with herring sperm DNA (Boehringer Mannheim, final concentration 20-200 μg/mL) and the mixture is boiled for three minutes and quickly chilled on ice. 400 ng of BUdR-labeled probe in 4X SC is added and the mixture (final vol=50 μL) is incubated at 65° C. for six to twenty hours in a tightly sealed siliconized 1.5 mL Eppendorf tube. After hybridization is complete, BSA (final concentration 1%), goat anti-biotin IgG (approximately 3 μg ), fluorescein-conjugated rabbit anti-goat IgG (approximately 3 μg ) and monomer-conjugated monoclonal anti-BUdR (2-100 μg/mL) are added to a final volume of 100 μL. After incubating the above mixture at 37° C. for 10-30 minutes, polymerization is carried out as described in Example III C above. In the presence of adenoviral DNA, fluorescence is incorporated into the polymer particles. When adenoviral DNA is replaced by salmon sperm DNA, substantially less fluorescence is incorporated. Similarly, when monomer-conjuqated anti-BUdR antibody is omitted, substantially less fluorescence is seen to be incorporated.

EXAMPLE V

Analyte Association Assay

An assay is performed to determine the presence of a specific protein-nucleic acid interaction, namely binding of the p19 protein of Rous sarcoma virus (RSV) to a specific site in the RSV genome.

A: Synthesis and Monomerization of Analyte Detecting Sequence

A synthetic oligonucleotide having the following sequence was synthesized on an automated DNA synthesizer (Applied Biosystems, Inc., Foster City, Calif.):
5' TCAATCTCTTCCTAGGATAC 3'
This oligonucleotide is complementary to nucleotides 2430-2449 of the RSV genome (Schwartz et al., Cell 32:853, 1983). p19 is known to bind 3' to this region, at approximately nucleotides 2396-2408 (Darlix et al., J. Mol. Biol. 160:147, 1982).

The oligonucleotide synthesized above is phosphorylated at its 5' end with [γ-$^{32}$P]-ATP and polynucleotide kinase, as described in Example III above. It is then reacted with 1,4-diaminobutane and carbodiimide (EDC) to form the phosphoramidate derivative, which is then reacted with the NHS-ester of methacrylic acid (as described in Example III above) to yield a probe having a single monomer group attached thereto. The monomerized oligomer is ethanol precipitated twice and the resultant pellet dissolved in water and stored at −20° C.

B: Fluorescein Labeling of Anti-p19 Antibody

An IgG fraction of affinity-purified rabbit anti-p19 antibody is fluoresceinated as follows: Thirty micrograms of FITC isomer II (20 μL of a 3.0 mg/mL solution in DMSO) is added to 1 mg of antibody in 125 μL of 0.27M carbonate buffer, pH 9.3. The mixture is incubated for 30 minutes at 37° C., after which free (unconjugated) fluorescein is separated from fluoresceinated antibody by gel filtration on Sephadex G25 equilibrated in 50 mM sodium phosphate, 0.5M NaCl, and 0.1% azide.

C: Preparation of RSV RNA

RSV, Prague C strain, is obtained from University Laboratories, Highland Park, N.J. Virus suspensions are prepared to contain $10^{11}$–$10^{12}$ particles/mL (0.15–1.5 mg virus) in 50 mM Tris HCl, pH 7.5/75 mM NaCl/1 mM EDTA. 0.4 mL aliquots are irradiated in plastic petri dishes using a 15 W ultraviolet light (252 nm) for 5 minutes to crosslink p19 to the viral RNA. Virus suspensions from twenty such plates are then pooled and lysed by the addition of 0.8 mL SDS (10% w/v). After a ten minute incubation at 37° C., 8 mL of 20 mM Tris HCl, pH 7.5/1 M LiCl/2 mM EDTA is added. The resultant mixture is chromatographed on a column of oligo dTcellulose (0.25 g dry weight) at room temperature. The column is washed first with 10 mM Tris HCl, pH 7.5/500 mM LiCl/1 mM EDTA/0.1% (w/v) SDS and then with 10 mM Tris HCl, pH 7.5/1 mM EDTA/0.1% (w/v) SDS to elute the bound poly-(A)-containing 70S viral RNA. The RNA is ethanol precipitated overnight and the precipitate collected by centrifugation at 12,000×g for 15 minutes. The precipitate is resuspended in water, made 0.3M in sodium acetate, and again ethanol precipitated. After washing once with ethanol, the RNA precipitate is dried in vacuo, redissolved in water, and stored at −20° C.

D: Partial Fragmentation of RSV 70S RNA

Fifty μg of RSV 70S RNA is dissolved in 90 μL 50 mM Tris-HCl, pH 8.2 and heated to 90° C. for 1-2 minutes, chilled on ice, and mixed with 5 μL of micrococcal nuclease (200 μg/mL) and 5 μL of CaCl$_2$ (20 mM). The fragmentation reaction is allowed to proceed at 37° C. for 15-30 minutes and then 5 μL of 50 mM EGTA (neutralized with KOH). The mixture is heated at 90° C. for several minutes, chilled on ice and stored at −20° C. To determine the distribution of fragment size, the fragements are labeled with $^{32}P$ and analyzed by gel electrophoresis. The labeled fragments are dissolved in 30 μL 5M urea, containing 0.025% BP and 0.025% XC; heated at 90° C. for 1 minute, and analysed on a 0.15×20×40 cm 8% polyacrylamide gel (30:1 crosslinked) containing 50 mM Tris borate, pH 8.3/1 mM EDTA/7M urea. The run is terminated after the BPB has migrated approximately 32 cm from the origin and the size of the fragments is determined by comparison with molecular weight standards included on the same gel.

Ideally, the fragments are 100 to 200 nucleotides in length. However, different commercial preparations of micrococcal nuclease give different size fragments and therefore it may be necessary to alter the reaction conditions to achieve the desired size.

E: Assay for p19 Binding to RSV-RNA

The partially fragmented RSV-RNA (10 μg in 20 μL) is mixed with 30 μL of 20 mM Tris HCl, pH 8.0, heated for one minute at 70° C., and then chilled on ice. 50 ng of monomerized probe prepared in (A) above is added to the fragmented RSV-RNA (prepared in (D) above) in 50 μL of 12X NET buffer containing 40 μg yeast tRNA. This mixture is incubated at 50° C. for 4-8 hours in a tightly sealed siliconized 1.5 mL Eppendorf tube and then chilled on ice. Fluoresceinated anti-p19 antibody (20 μL of a 250 μg/mL solution) is added and the mixture is incubated at 37° C. for 1 hour. Then the mixture is cooled to room temperature and HEMA is added to a final concentration of 1%. 5 μL of 0.8 M TEMED in 0.1M sodium borate, pH 7.0, is added, followed by 5 μL of 0.1M ammonium persulfate. The resultant solution is mixed rapidly and allowed to polymerize for ten minutes at 37° C. The mixture is diluted with 1 mL of water and analyzed by flow cytometry. Under these conditions, fluorescence is seen to be incorporated into the polymer particles.

Two controls are run in parallel. In the first control, the RSV-RNA is not UV-irradiated. In the second control, E. coli ribosomal RNA is substituted for RSV-RNA. In both cases there is substantially less incorporation of fluorescence into the polymer particles, indicating that both p19 and RSV-RNA are required for incorporation of reporter into the polymer.

Although the foregoing invention has been described in some detail by way of illustration and example for purposes of clarity of understanding, it will be obvious that certain changes and modifications may be practiced within the scope of the appended claims.

We claim:

1. A method employing recognition pairs of reactants for determining the presence or amount of an analyte in a sample suspected of containing said analyte, comprising:
    (a) labeling a first recognition reactant capable of specifically binding to the analyte with either of an addition polymerizable organic monomer or reporter;
    (b) contacting the sampel with the labeled reactant to form a first recognition reactant-analyte complex;
    (c) labeling a second recognition reactant capable of specifically binding to the analyte with the alternative label not used for the first recognition reactant;
    (d) contacting the sample either sequentially or simultaneously with the labeled second reactant to form a first recognition reactant-analyte-second recognition reactant ternary complex;
    (e) separating the resultant ternary complex from free reporter-labeled recognition reactant by initiating polymerization of the monomer-labeled recognition reactant in the presence of an unlabeled addition polymerizable organic monomer; and
    (f) detecting the incorporation of reporter-labeled recognition reactant into said polymerized ternary complex and relating this incorporation to the analyte present in the sample.

2. A method employing recognition pairs of reactants for determining the presence or amount of a nucleic acid analyte in a sample suspected of containing said analyte comprising:
    (a) labeling as a first recognition reactant a first single stranded polynucleotide probe capable of specifically binding to the analyte with either of an addition polymerizable organic monomer or reporter;
    (b) contacting the sample with the labeled first probe to form a first probe-analyte complex;
    (c) labeling as a second recognition reactant a second single stranded polynucleotide probe capable of specifically binding to the analyte with the alternative label not used for the first probe;
    (d) contacting the sample sequentially or simultaneously with the labeled second probe to form a first probe-analyte-second probe ternary complex;
    (e) separating the resultant ternary complex from free reporter-labeled probe by initiating polymerization of the monomer-labeled probe in the presence of an unlabeled addition polymerizable organic monomer; and
    (f) detecting the incorporation of reporter-labeled probe into said polymerized ternary complex to determine the presence of the analyte.

3. A method for detecting the presence or amount of association between two analytes in a sample suspected of containing both analytes comprising:
    (a) labeling a first recognition reactant capable of specifically binding to a first analyte with either of addition polymerizable monomer or reporter;
    (b) contacting said sample with the labeled first recognition reactant to form a first recognition reactant-first analyte complex;
    (c) labeling a second recognition reactant capable of specifically binding to the second analyte with the alternative label not used for the first recognition reactant;
    (d) contacting said sample sequentially or simultaneously with the labeled second reactant to form a second recognition reactant-second analyte complex;
    (e) initiating polymerization of the monomer-labeled recognition reactant whereby the first complex is separated from the second complex unless they are associated; and
    (f) detecting the incorporation of reporter-labeled recognition reactant into said polymerized complex to determine the presence or amount of analyte association.

4. A method for determining the presence or amount of an analyte in a sample suspected of containing said analyte comprising:
    (a) labeling analyte with either of an addition polymerizable organic monomer or reporter;

(b) contacting the sample with the labeled analyte to form a mixture;

(c) labeling a recognition reactant capable of specifically binding to the analyte or the labeled analyte with the alternative label not used in step (a);

(d) contacting the mixture with the labeled recognition reactant to form recognition reactant-analyte complex;

(e) separating monomer-containing recognition reactant-analyte complex from recognition reactant-analyte complex not labeled with monomer by initiating polymerization of the monomer-labeled reactant in the presence of an unlabeled addition polymerizable organic monomer; and (f) detecting the incorporation of reporter into said polymerized complex and relating this incorporation to the analyte present in the sample.

5. A method employing recognition pairs of reactants for determining the presence or amount of a nucleic acid analyte in a sample suspected of containing said analyte, comprising:

(a) labeling a first antibody reactant capable of specifically binding to the nucleic acid analyte with either of an addition polymerizable organic monomer or reporter;

(b) contacting the sample with the labeled reactant to form an antibody reactant-analyte complex;

(c) labeling a nucleic acid probe capable of specifically binding to the nucleic acid analyte with the alternative label not used for the antibody reactant;

(d) contacting the sample either sequentially or simultaneously with the nucleic acid probe to form an antibody reactant-analyte-nucleic acid probe ternary complex;

(e) separating the resultant ternary complex from free reporter-labeled recognition reactant by initiating polymerization of the monomer-labeled recognition reaction; and (f) detecting the incorporation of reporter-labeled recognition reactant into said polymerized ternary complex and relating this incorporation to the analyte present in the sample.

6. A method employing recognition pairs of nucleic acids for determining the presence or amount of a nucleic acid analyte in a sample suspected of containing said analyte, comprising:

(a) labeling as a first recognition reactant a first single stranded polynucleotide probe capable of specifically binding to the analyte with either of an addition polymerizable organic monomer or reporter;

(b) contacting the sample with the labeled reactant to form a first probe-analyte complex;

(c) labeling as a second recognition reactant a second single stranded polynucleotide probe capable of specifically binding to the analyte with the alternative label not used for the first probe;

(d) contacting the sample either sequentially or simultaneously with the labeled second probe to form a first probe-analyte-second probe ternary complex;

(e) separating the resultant ternary complex from free reporter-labeled probe by initiating polymerization of the monomer-labeled probe; and (f) detecting the incorporation of reporter-labeled probe into said polymerized ternary complex and relating this incorpration to the analyte present in the sample.

7. The method of claim 4 further comprising adding unlabeled addition polymerizable addition monomer to the sample and thereafter initiating copolymerization of the monomer-labeled reactant and unlabeled monomer, whereby the ternary complex is separated from free reporter-labeled reactant.

8. A method as recited in any one of claims 1, 2, 4, or 7 wherein the free monomer is at least one member selected from the group consisting of molecules containing olefinic unsaturation or acetylenic unsaturation.

9. The method of claim 8 wherein the monomer is polyunsaturated.

10. The method of claim 9 wherein the polyunsaturated monomer is selected from the group consisting of monomers, oligomers and polymers.

11. A method as recited in any one of claims 1, 2, 3, or 4 wherein the monomer label is at least one member selected from the group consisting of molecules containing olefinic unsaturation and at least one reactable site.

12. The method of claim 11 wherein the monomer is polyunsaturated.

13. The method of claim 12 wherein the polyunsaturated monomer is selected from the group consisting of monomers, oligomers and polymers.

14. A method as recited in any one of claims 1, 2, 3, or 4 wherein the reporter is selected from the group consisting of fluorophores, chromophores, chemiluminescence source materials, radioisotopes, and enzymes.

15. A method as recited in any one of claims 1, 2, 3, or 4 wherein the recognition pairs are selected from the group consisting of antigen/antibody, hormone/receptor, drug/receptor, nucleic acid/complementary nucleic acid, lectin/sugar, enzyme/cofactor, enzyme/substrate, enzyme/product, enzyme/inhibitor, antibody/receptor, vitamin/transport protein, virus/receptor, cell/receptor, growth factor/receptor and chelating agent/ion.

16. The method of claim 1 wherein said analyte is an antigen and the first and second recognition reactants are antibodies directed to different determinants on the analyte.

17. The method of claim 1 wherein said analyte is an antigen and the first and second recognition reactants are antibodies directed to the same determinant on the analyte.

18. A method as recited in any one of claims 1, 2, 3, or 4 wherein the monomer label is at least one member selected from the group consisting of molecules containing acetylenic unsaturation and at least one reactable site.

19. A method as recited in claim 2 or 6 further comprising fragmenting the nucleic acid analyte prior to contact with the first probe.

20. The method of claim 19 wherein the analyte is fragmented by at least one procedure selected from the group consisting of mechanical shearing, enzymatic digestion, sonication, irradiation, and chemical cleavage.

21. A method as recited in claim 2 wherein the first and second probes are synthetically, post-synthetically or indirectly labeled.

22. A method as recited in claim 2 wherein at least one of the first and second probes is complementary to the analyte over substantially the entire probe sequence.

23. The method of claim 21 wherein the label for each indirectly labeled probe is provided by a labeled antibody.

24. The method of claim 3 wherein the first and second analytes are proteins.

25. The method of claim 3 wherein the second analyte is the first analyte-first recognition reactant complex.

26. The method of claim 3 wherein the first and second analytes are nucleic acids.

27. The method of claim 3 wherein one analyte is a nucleic acid and the other analyte is a protein.

28. The method of any one of claims 24, 26 or 27 wherein the analytes are associated by covalent bonds.

29. The method of any one of claims 24, 26 or 27 wherein the analytes are associated by non-covalent bonds.

30. The method of claim 25 wherein the first analyte-first recognition reactant complex is comprised of complementary nucleic acid sequences.

31. The method of claim 25 wherein the first analyte-first recognition reactant complex is comprised of an antigen and an antibody.

32. The method of claim 25 wherein the first analyte-first recognition reactant complex is comprised of a nucleic acid and a protein.

33. The method of claim 28 wherein the covalent bonds are selected from the group consisting of phosphodiester bonds and peptide bonds.

34. The method of claim 29 wherein the non-covalent bonds are selected from the group consisting of hydrogen bonds, hydrophobic bonds, ionic and polar bonds.

35. The method of any one of claims 26, 27, or 30 further comprising fragmenting at least one of the nucleic acid analytes prior to contact with the first recognition reactant.

* * * * *